United States Patent
Wacker et al.

(10) Patent No.: US 10,195,262 B2
(45) Date of Patent: Feb. 5, 2019

(54) **PREVENTION OF *STAPHYLOCOCCUS AUREUS* INFECTIONS BY GLYCOPROTEIN VACCINES SYNTHESIZED IN *ESCHERICHIA COLI***

(71) Applicant: GLAXOSMITHKLINE BIOLOGICALS SA, Rixensart (BE)

(72) Inventors: Michael Wacker, Unterengstringen (CH); Michael Kowarik, Zurich (CH); Michael Wetter, Zurich (CH)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 15/101,626

(22) PCT Filed: Dec. 3, 2014

(86) PCT No.: PCT/EP2014/076468
§ 371 (c)(1),
(2) Date: Jun. 3, 2016

(87) PCT Pub. No.: WO2015/082571
PCT Pub. Date: Jun. 11, 2015

(65) Prior Publication Data
US 2016/0303213 A1      Oct. 20, 2016

Related U.S. Application Data

(60) Provisional application No. 61/911,919, filed on Dec. 4, 2013.

(51) Int. Cl.
*A61K 39/085*  (2006.01)
*A61K 39/40*   (2006.01)
*A61K 39/00*   (2006.01)

(52) U.S. Cl.
CPC .......... *A61K 39/085* (2013.01); *A61K 39/40* (2013.01); *A61K 2039/55505* (2013.01); *A61K 2039/6037* (2013.01); *Y02A 50/474* (2018.01)

(58) Field of Classification Search
CPC .... A61K 39/116; A61K 39/085; A61K 47/48; A61K 35/76; A61K 39/05; A61K 39/08;
(Continued)

(56) References Cited

U.S. PATENT DOCUMENTS

2007/0141077 A1*  6/2007  Pavliak ............... A61K 39/085
                                                              424/203.1

FOREIGN PATENT DOCUMENTS

WO    2004/080490 A2    9/2004
WO    2007/071692 A2    6/2007
(Continued)

OTHER PUBLICATIONS

Overcoming Challenges in *S. aureus* Vaccine Development Meeting Summary. National Institue of Allergy and Infectious Diseases. Rockville, Md Jun. 7, 2013.*
(Continued)

*Primary Examiner* — Jana A Hines

(57) ABSTRACT

Provided herein are immunogenic compositions and vaccines for the treatment and prevention of *Staphylococcus aureus* infections. These immunogenic compositions and vaccines comprise combinations of bioconjugates capsular polysaccharides that are N-linked to one or more carrier proteins.

8 Claims, 14 Drawing Sheets

Specification includes a Sequence Listing.

(58) Field of Classification Search
CPC ...... A61K 39/09; A61K 39/095; A61K 39/10; A61K 39/102; A61K 39/13; A61K 39/29; A61K 39/295; A61K 39/385; A61K 39/39; C07K 14/31; A61P 31/00
See application file for complete search history.

(56) References Cited

FOREIGN PATENT DOCUMENTS

| WO | 2007/113223 A2 | 10/2007 | |
|---|---|---|---|
| WO | 2011/138361 A1 | 11/2011 | |
| WO | WO 2011/138361 | * 11/2011 | ........... A61K 39/085 |
| WO | WO 2012085872 | * 6/2012 | ........... A61K 39/085 |

OTHER PUBLICATIONS

Wardenburg et al., Vaccine protection against *Staphylococcus aureus* pneumonia, The Journal of Experimental Medicine, vol. 205, No. 2, Feb. 18, 2008, p. 287-294.

* cited by examiner

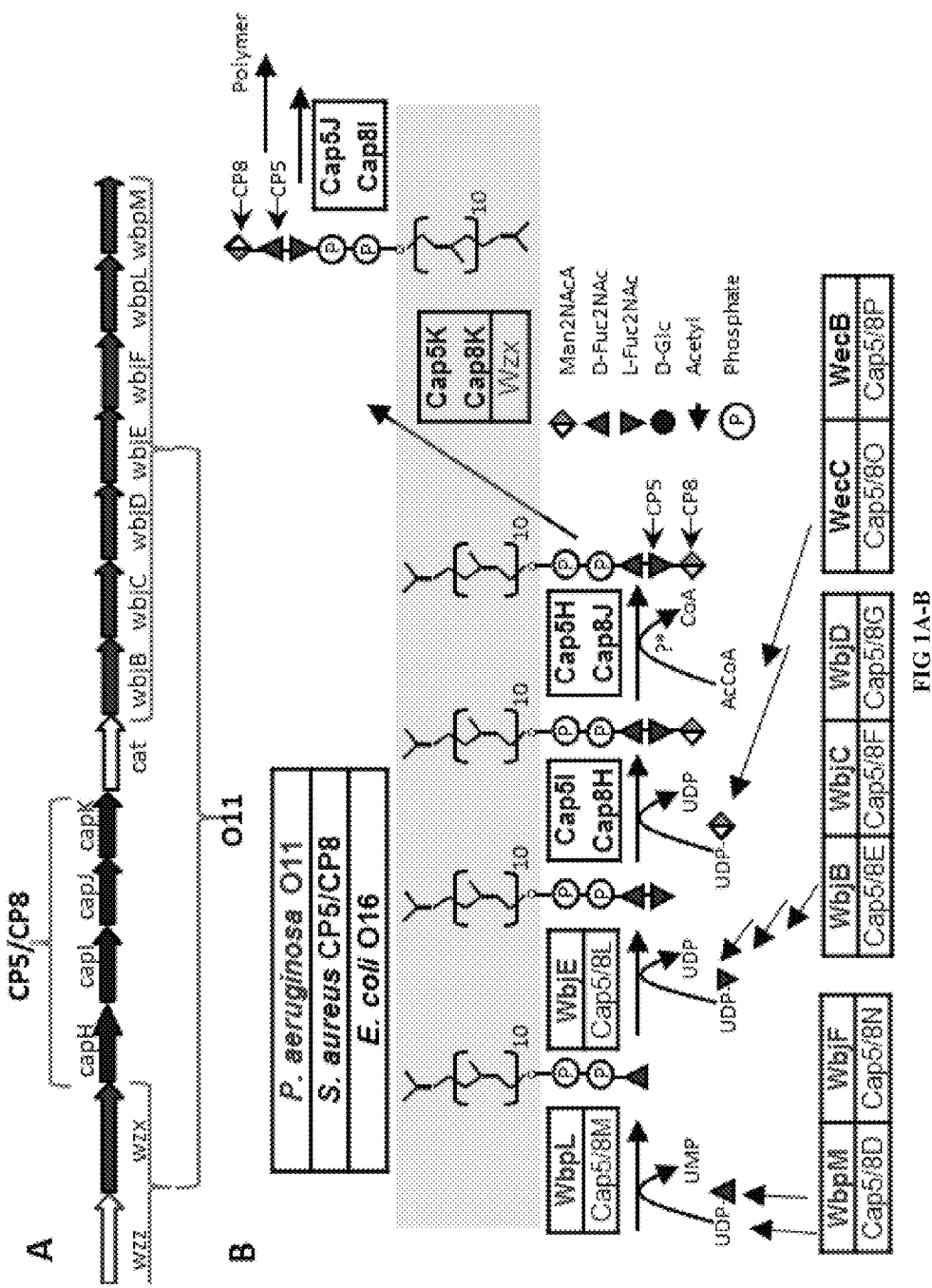
FIG 1A-B

FIG 2A-B

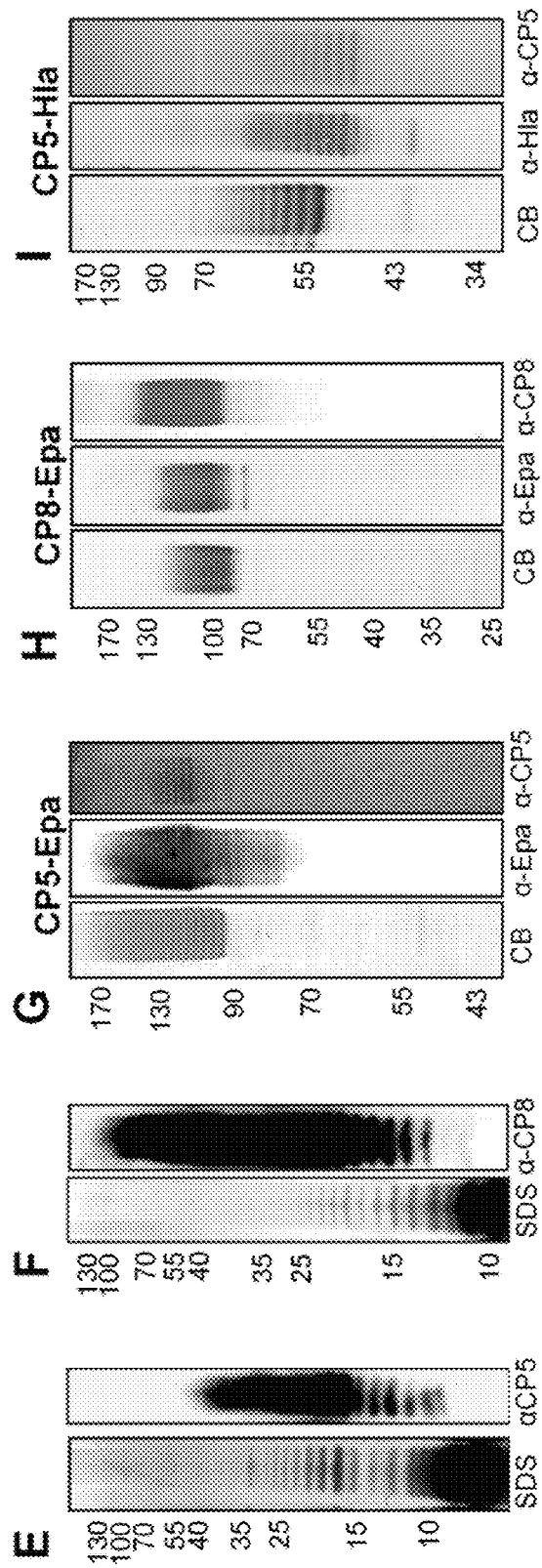
FIG 2E-I

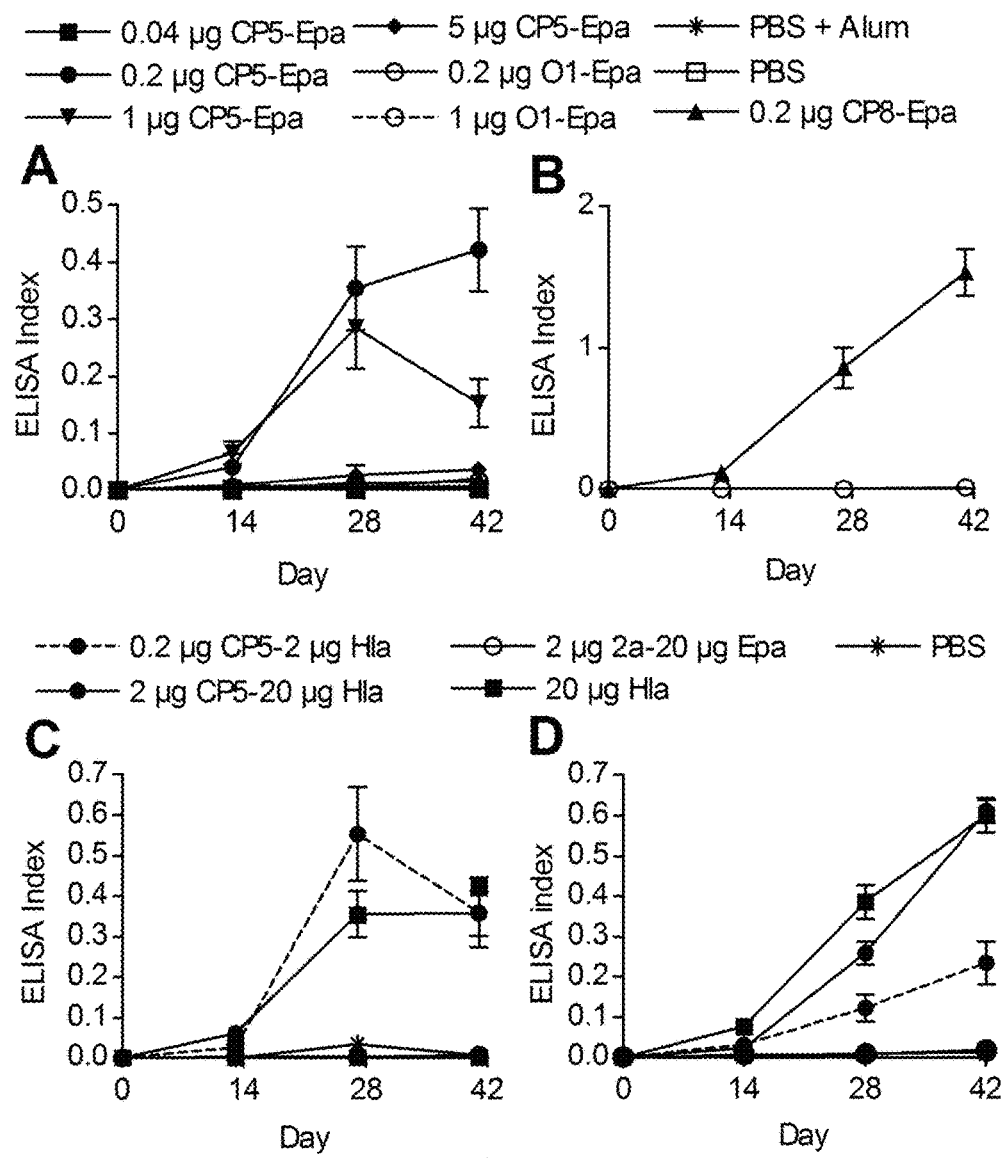
FIG 3A-D

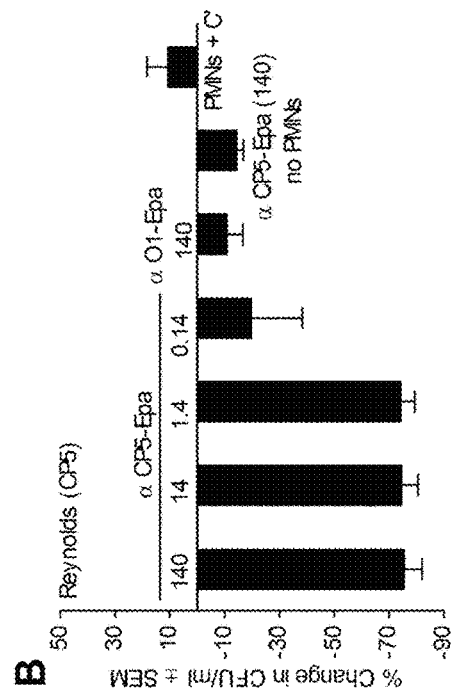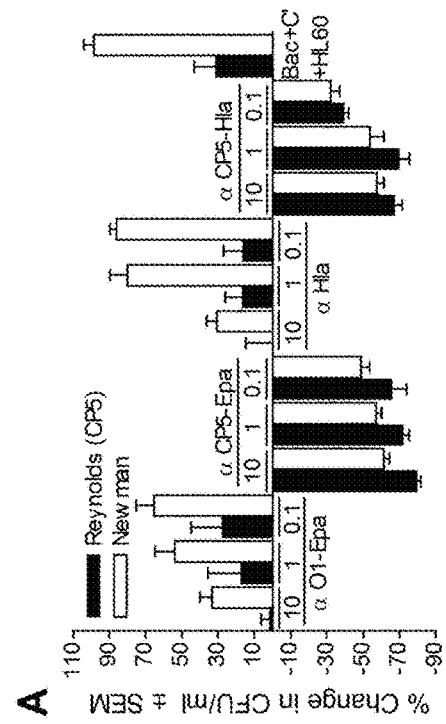
FIG 4A-B

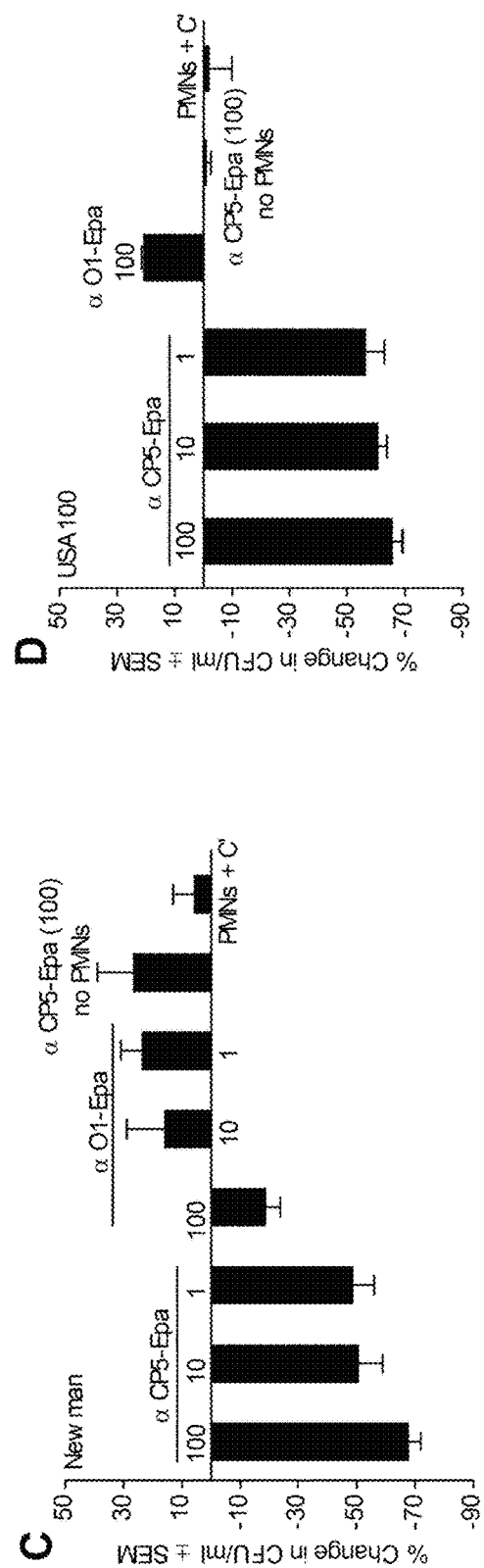
FIG 4C-D

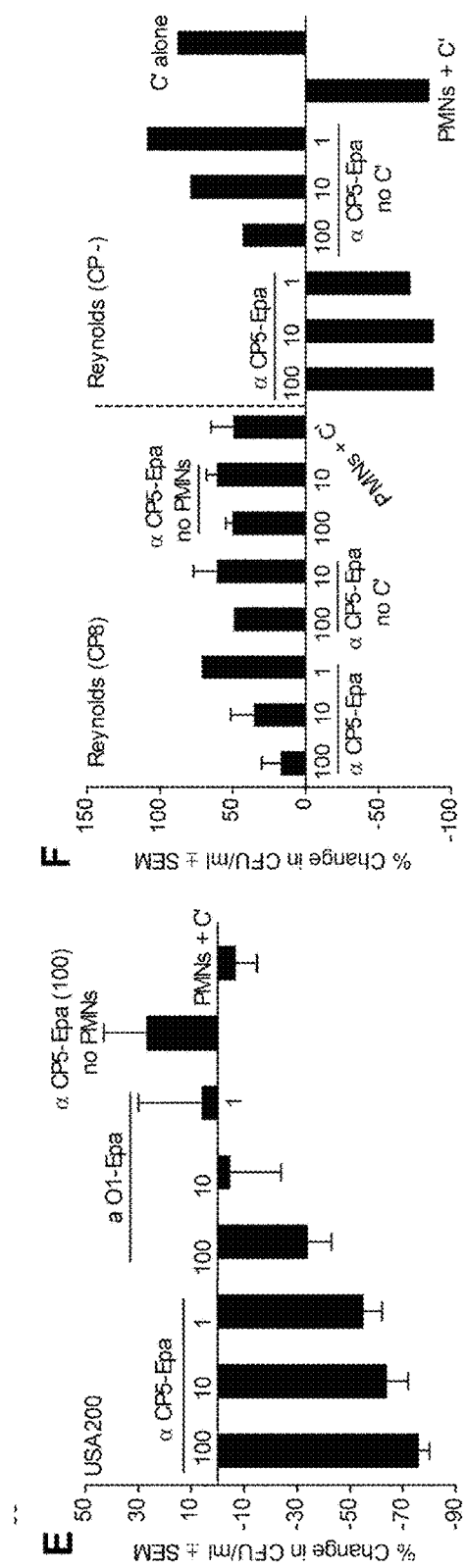
FIG 4E-F

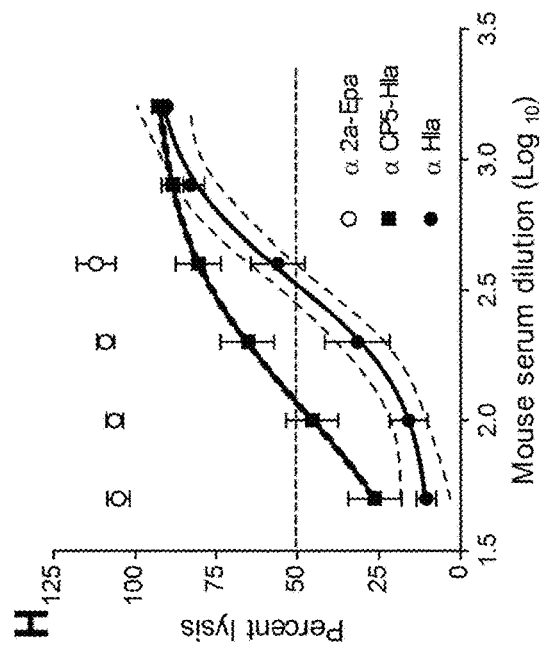
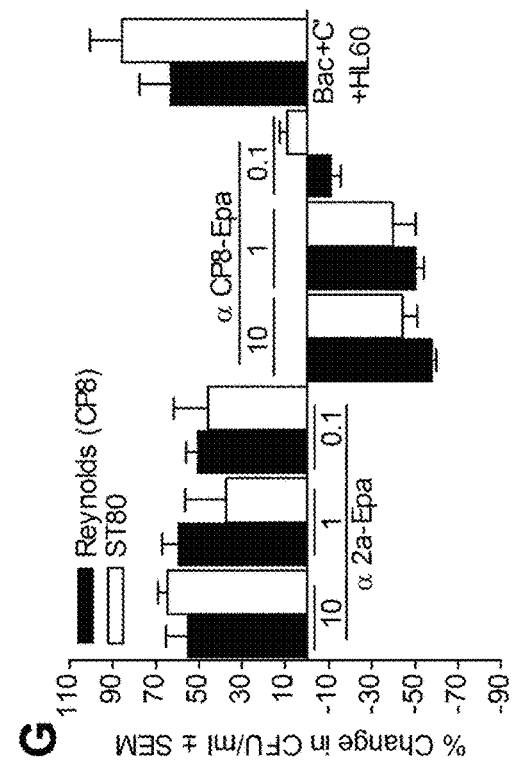
FIG 4G-H

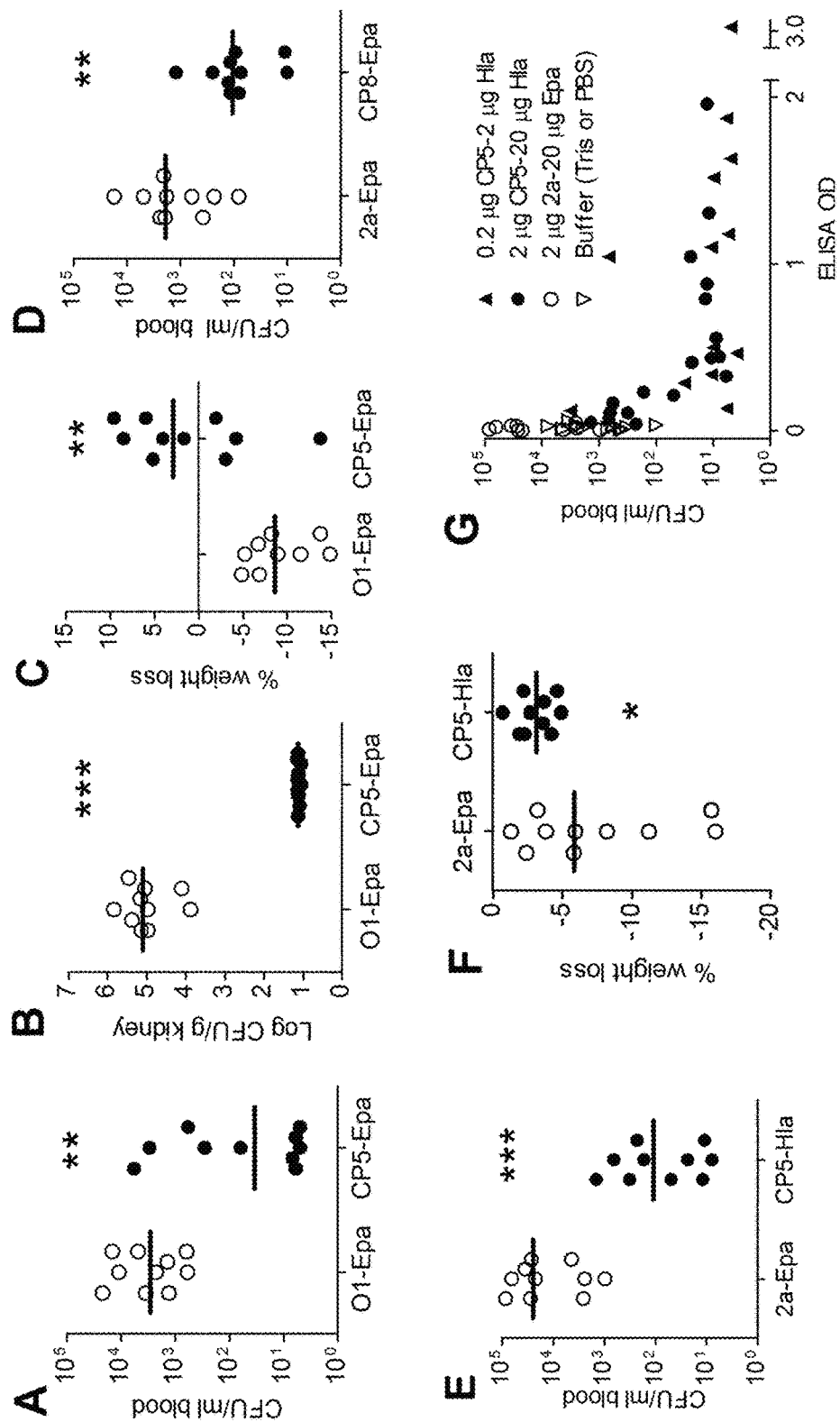
FIG 5A-G

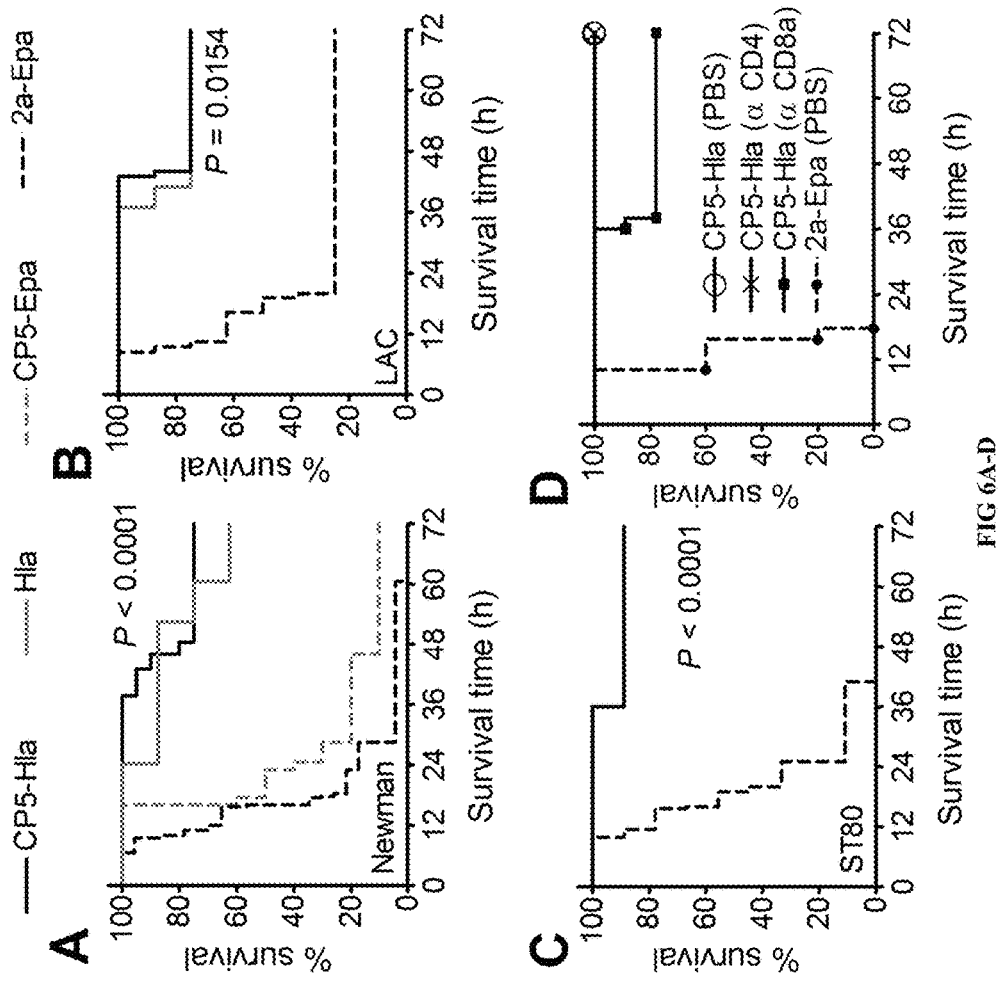
FIG 6A-D

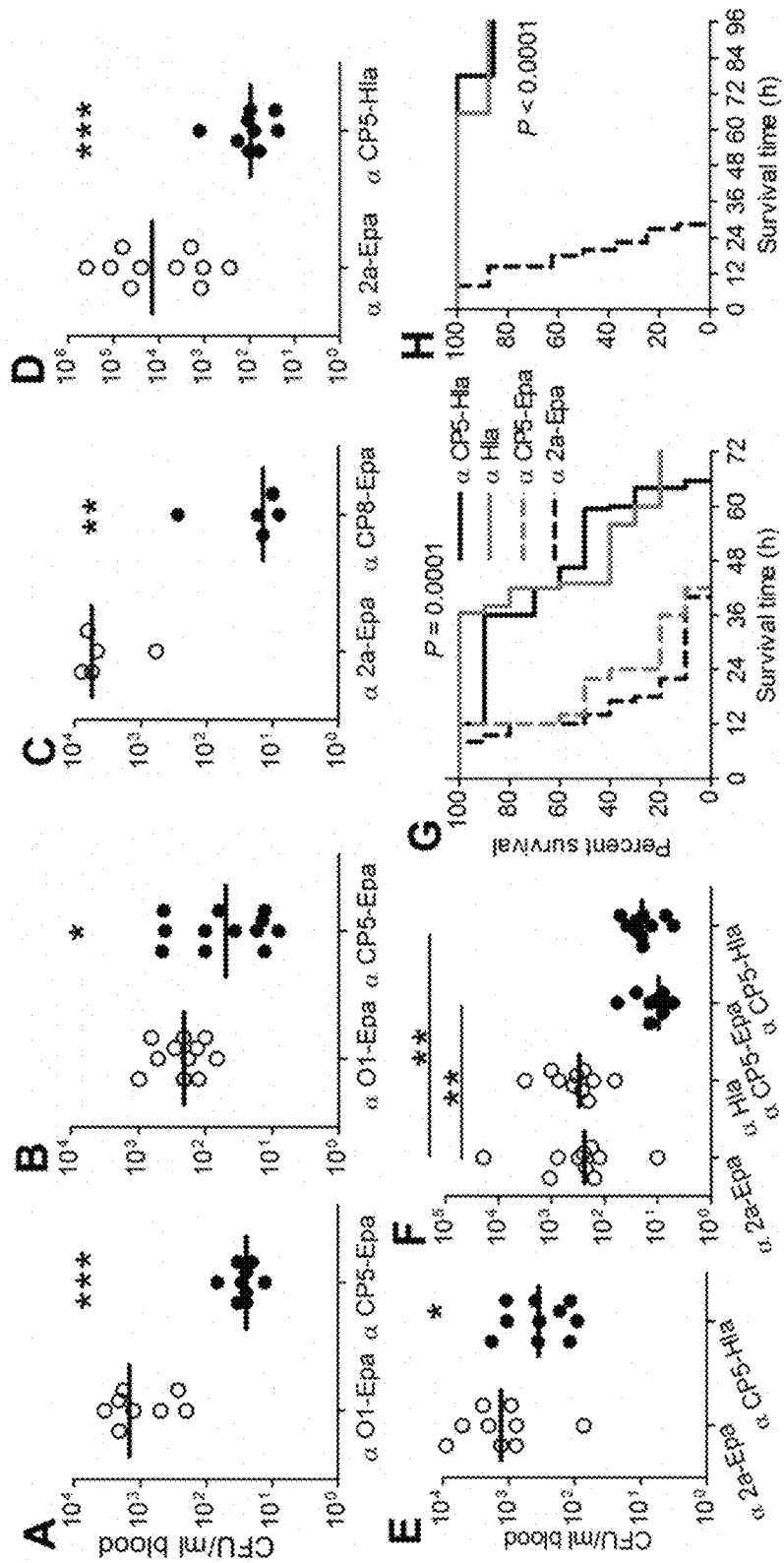
FIG 7A-H

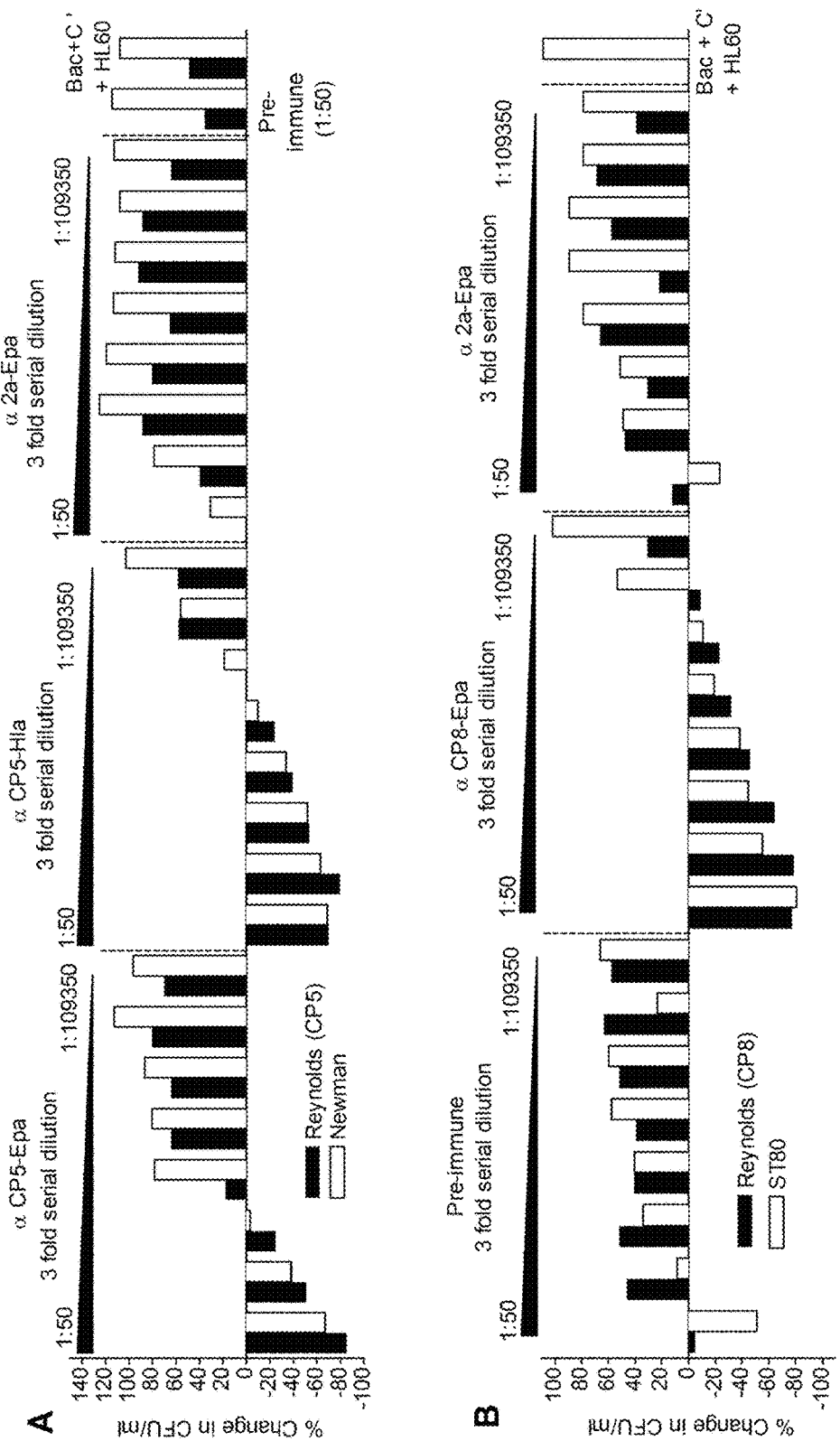
FIG 8A-B

SEQUENCE LISTING

<160> NUMBER OF SEQ ID NOS: 53

<210> SEQ ID NO 1
<211> LENGTH: 23
<212> TYPE: PRT
<213> ORGANISM: Artificial Sequence
<220> FEATURE:
<223> OTHER INFORMATION: N terminus sequence of Epa expression construct

```
<400> SEQUENCE: 1

Met Lys Lys Ile Trp Leu Ala Leu Ala Gly Leu Val Leu Ala Phe Ser
1               5                   10                  15

Ala Ser Ala Ala Glu Glu Ala
            20

<210> SEQ ID NO 2
<211> LENGTH: 87
<212> TYPE: DNA
<213> ORGANISM: Artificial Sequence
<220> FEATURE:
<223> OTHER INFORMATION: primer P1-F

<400> SEQUENCE: 2
attaatgaaa aagatttggc tggcgctggc tggtttagtt ttagcgttta gcgctagcgc      60
gtacccatac gacgtcccag actacgc                                         87

<210> SEQ ID NO 3
<211> LENGTH: 34
<212> TYPE: DNA
<213> ORGANISM: Artificial Sequence
<220> FEATURE:
<223> OTHER INFORMATION: primer P1-R

<400> SEQUENCE: 3
agaattctta aacactggcg tcaaagtgga cagg                                 34

<210> SEQ ID NO 4
<211> LENGTH: 30
<212> TYPE: DNA
<213> ORGANISM: Artificial Sequence
<220> FEATURE:
<223> OTHER INFORMATION: primer P2-F

<400> SEQUENCE: 4
aagctagcgc cgccgaggaa gccttcgacc                                      30

<210> SEQ ID NO 5
<211> LENGTH: 50
<212> TYPE: DNA
<213> ORGANISM: Artificial Sequence
<220> FEATURE:
<223> OTHER INFORMATION: primer P2-R

<400> SEQUENCE: 5
aagaattctc agtggtggtg gtggtggtgc ttcaggtcct cgcgcggcgg                50

<210> SEQ ID NO 6
<211> LENGTH: 27
<212> TYPE: DNA
<213> ORGANISM: Artificial Sequence
<220> FEATURE:
<223> OTHER INFORMATION: primer P3-F

<400> SEQUENCE: 6
gaaggcgggc gcgtgaccat tctcggc                                         27

<210> SEQ ID NO 7
<211> LENGTH: 27
<212> TYPE: DNA
<213> ORGANISM: Artificial Sequence
<220> FEATURE:
<223> OTHER INFORMATION: primer P3-R

<400> SEQUENCE: 7
```
gccgagaatg gtcacgcgcc cgccttc                                               27

<210> SEQ ID NO 8
<211> LENGTH: 26
<212> TYPE: DNA
<213> ORGANISM: Artificial Sequence
<220> FEATURE:
<223> OTHER INFORMATION: primer P4-R

<400> SEQUENCE: 8
ccgcgcattc cccggggcag gtcagg                                                26

<210> SEQ ID NO 9
<211> LENGTH: 26
<212> TYPE: DNA
<213> ORGANISM: Artificial Sequence
<220> FEATURE:
<223> OTHER INFORMATION: primer P4-R

<400> SEQUENCE: 9
cctgacctgc ccgggaat gcgcgg                                                  26

<210> SEQ ID NO 10
<211> LENGTH: 27
<212> TYPE: DNA
<213> ORGANISM: Artificial Sequence
<220> FEATURE:
<223> OTHER INFORMATION: primer P5-F

<400> SEQUENCE: 10
tttagttcta ttttgatctt tggcgac                                               27

<210> SEQ ID NO 11
<211> LENGTH: 27
<212> TYPE: DNA
<213> ORGANISM: Artificial Sequence
<220> FEATURE:
<223> OTHER INFORMATION: primer P5-R

<400> SEQUENCE: 11
gtcgccaaag atcaaaatag aactaaa                                               27

<210> SEQ ID NO 12
<211> LENGTH: 55
<212> TYPE: DNA
<213> ORGANISM: Artificial Sequence
<220> FEATURE:
<223> OTHER INFORMATION: primer P6-F

<400> SEQUENCE: 12
catgacctgg acatcaagga taataataat tctactccca cggtcatcag tcatc              55

<210> SEQ ID NO 13
<211> LENGTH: 55
<212> TYPE: DNA
<213> ORGANISM: Artificial Sequence
<220> FEATURE:
<223> OTHER INFORMATION: primer P6-R

<400> SEQUENCE: 13
gatgactgat gaccgtggga gtagaattat tattatcctt gatgtccagg tcatg              55

<210> SEQ ID NO 14
<211> LENGTH: 31
<212> TYPE: DNA

```
<213> ORGANISM: Artificial Sequence
<220> FEATURE:
<223> OTHER INFORMATION: primer P7-F

<400> SEQUENCE: 14
aattcacatg tgtgcacctt aagcctcagg g                              31

<210> SEQ ID NO 15
<211> LENGTH: 31
<212> TYPE: DNA
<213> ORGANISM: Artificial Sequence
<220> FEATURE:
<223> OTHER INFORMATION: primer P7-R

<400> SEQUENCE: 15
aattccctga ggcttaaggt gcacacatgt g                              31

<210> SEQ ID NO 16
<211> LENGTH: 37
<212> TYPE: DNA
<213> ORGANISM: Artificial Sequence
<220> FEATURE:
<223> OTHER INFORMATION: primer P8-F

<400> SEQUENCE: 16
ctgcctgagg caattcttct ttgatgacgg ctgatgg                        37

<210> SEQ ID NO 17
<211> LENGTH: 39
<212> TYPE: DNA
<213> ORGANISM: Artificial Sequence
<220> FEATURE:
<223> OTHER INFORMATION: primer P8-R

<400> SEQUENCE: 17
acgtacatgt tgcccatcca cgaaaccacc ttatcgccg                      39

<210> SEQ ID NO 18
<211> LENGTH: 43
<212> TYPE: DNA
<213> ORGANISM: Artificial Sequence
<220> FEATURE:
<223> OTHER INFORMATION: primer P9-F

<400> SEQUENCE: 18
gttagcgcta gcaggaggga cgatgaggat agcgattgaa aag                 43

<210> SEQ ID NO 19
<211> LENGTH: 67
<212> TYPE: DNA
<213> ORGANISM: Artificial Sequence
<220> FEATURE:
<223> OTHER INFORMATION: primer P9-R

<400> SEQUENCE: 19
catttctaga ttacgcataa tccggcacat catacggata actagtatcc tttttattta    60
aatattc                                                              67

<210> SEQ ID NO 20
<211> LENGTH: 92
<212> TYPE: DNA
<213> ORGANISM: Artificial Sequence
<220> FEATURE:
<223> OTHER INFORMATION: primer P10-F

<400> SEQUENCE: 20
```

```
ggggtaccag gaggtgtaca atgagaattt taaatattgt atcgaggggg taccaggagg    60
tgtacaatga gaattttaaa tattgtatcg ag                                  92
```

<210> SEQ ID NO 21
<211> LENGTH: 67
<212> TYPE: DNA
<213> ORGANISM: Artificial Sequence
<220> FEATURE:
<223> OTHER INFORMATION: primer P10-R

<400> SEQUENCE: 21

```
ccggatccca gatcctcttc tgagatgagt ttttgttcaa atttatataa ttctactaat    60
cgttcac                                                              67
```

<210> SEQ ID NO 22
<211> LENGTH: 45
<212> TYPE: DNA
<213> ORGANISM: Artificial Sequence
<220> FEATURE:
<223> OTHER INFORMATION: primer P11-F

<400> SEQUENCE: 22

```
cgtgttgcta gcaggaggaa ctatgaaatt ttttgtactt tgtgc                    45
```

<210> SEQ ID NO 23
<211> LENGTH: 62
<212> TYPE: DNA
<213> ORGANISM: Artificial Sequence
<220> FEATURE:
<223> OTHER INFORMATION: primer P11-R

<400> SEQUENCE: 23

```
ggcctttcta gattatttat catcatcatc tttataatca ccatgatgac gccgtccttt    60
tg                                                                   62
```

<210> SEQ ID NO 24
<211> LENGTH: 113
<212> TYPE: DNA
<213> ORGANISM: Artificial Sequence
<220> FEATURE:
<223> OTHER INFORMATION: primer P12-F

<400> SEQUENCE: 24

```
ggacgctggt cgttacagag gtctctttgg ggatgggaat gtttttcctg gccacggtta    60
agttgagaga gaaaagggga ctttgactta agatgaggat agcgattgaa aag          113
```

<210> SEQ ID NO 25
<211> LENGTH: 45
<212> TYPE: DNA
<213> ORGANISM: Artificial Sequence
<220> FEATURE:
<223> OTHER INFORMATION: primer P12-R

<400> SEQUENCE: 25

```
ctcattgtac acctcctgtt acgcataatc cggcacatca tacgg                    45
```

<210> SEQ ID NO 26
<211> LENGTH: 32
<212> TYPE: DNA
<213> ORGANISM: Artificial Sequence
<220> FEATURE:
<223> OTHER INFORMATION: primer P13-F

<400> SEQUENCE: 26
caggaggtgt acaatgagaa ttttaaatat tg                          32

<210> SEQ ID NO 27
<211> LENGTH: 78
<212> TYPE: DNA
<213> ORGANISM: Artificial Sequence
<220> FEATURE:
<223> OTHER INFORMATION: primer P13-R

<400> SEQUENCE: 27
ctaaggagga tattcatatg gtgcacggaa gtttaaactt atttatcatc atcatcttta    60
taatcaccat gatgacgc                                          78

<210> SEQ ID NO 28
<211> LENGTH: 25
<212> TYPE: DNA
<213> ORGANISM: Artificial Sequence
<220> FEATURE:
<223> OTHER INFORMATION: primer P14-F

<400> SEQUENCE: 28
ggacgctggt cgttacagag gtctc                                  25

<210> SEQ ID NO 29
<211> LENGTH: 78
<212> TYPE: DNA
<213> ORGANISM: Artificial Sequence
<220> FEATURE:
<223> OTHER INFORMATION: primer P14-R

<400> SEQUENCE: 29
ctaaggagga tattcatatg gtgcacggaa gtttaaactt atttatcatc atcatcttta    60
taatcaccat gatgacgc                                          78

<210> SEQ ID NO 30
<211> LENGTH: 20
<212> TYPE: DNA
<213> ORGANISM: Artificial Sequence
<220> FEATURE:
<223> OTHER INFORMATION: primer P15-F

<400> SEQUENCE: 30
catatgaata tcctccttag                                        20

<210> SEQ ID NO 31
<211> LENGTH: 101
<212> TYPE: DNA
<213> ORGANISM: Artificial Sequence
<220> FEATURE:
<223> OTHER INFORMATION: primer P15-R

<400> SEQUENCE: 31
cttcaaaacg gcatttccaa aggaaccagt tccaccggta attaacagaa cagagttctt    60
atccatacac cacctcttta cgtgtaggct ggagctgctt c                101

<210> SEQ ID NO 32
<211> LENGTH: 25
<212> TYPE: DNA
<213> ORGANISM: Artificial Sequence
<220> FEATURE:
<223> OTHER INFORMATION: primer P16-F

<400> SEQUENCE: 32
ggacgctggt cgttacagag gtctc                                          25

<210> SEQ ID NO 33
<211> LENGTH: 23
<212> TYPE: DNA
<213> ORGANISM: Artificial Sequence
<220> FEATURE:
<223> OTHER INFORMATION: primer P16-R

<400> SEQUENCE: 33
cttcaaaacg gcatttccaa agg                                            23

<210> SEQ ID NO 34
<211> LENGTH: 47
<212> TYPE: DNA
<213> ORGANISM: Artificial Sequence
<220> FEATURE:
<223> OTHER INFORMATION: primer P17-F

<400> SEQUENCE: 34
acgagtttaa acaggaggca tcatggttaa gaaagttttt attatgg                  47

<210> SEQ ID NO 35
<211> LENGTH: 65
<212> TYPE: DNA
<213> ORGANISM: Artificial Sequence
<220> FEATURE:
<223> OTHER INFORMATION: primer P17-R

<400> SEQUENCE: 35
ccgcgtgcac ttacgcataa tccggcacat catacggata actatcgacg tcctttttat    60
taatg                                                                65

<210> SEQ ID NO 36
<211> LENGTH: 35
<212> TYPE: DNA
<213> ORGANISM: Artificial Sequence
<220> FEATURE:
<223> OTHER INFORMATION: primer P18-F

<400> SEQUENCE: 36
aggtacatgt cgcgaaggta aagtcagccg cattg                               35

<210> SEQ ID NO 37
<211> LENGTH: 40
<212> TYPE: DNA
<213> ORGANISM: Artificial Sequence
<220> FEATURE:
<223> OTHER INFORMATION: primer P18-R

<400> SEQUENCE: 37
ttgctagcgc tgtcgcttat catgtagcgc ttaaatagcc                          40

<210> SEQ ID NO 38
<211> LENGTH: 101
<212> TYPE: DNA
<213> ORGANISM: Artificial Sequence
<220> FEATURE:
<223> OTHER INFORMATION: primer P19-F

<400> SEQUENCE: 38
acatgataag cgacagcgct agcaatcaaa tcttttaaag ttacttctca ggaatagtaa    60
aaggaggaca gctatgttga aaaagagta tttaaaaaac c                         101

<210> SEQ ID NO 39
<211> LENGTH: 42
<212> TYPE: DNA
<213> ORGANISM: Artificial Sequence
<220> FEATURE:
<223> OTHER INFORMATION: primer P19-R

<400> SEQUENCE: 39
cggcggacat gtttaagcgt aatctggaac atcgtatggg ta        42

<210> SEQ ID NO 40
<211> LENGTH: 35
<212> TYPE: DNA
<213> ORGANISM: Artificial Sequence
<220> FEATURE:
<223> OTHER INFORMATION: primer P20-F

<400> SEQUENCE: 40
aggtacatgt cgcgaaggta aagtcagccg cattg        35

<210> SEQ ID NO 41
<211> LENGTH: 42
<212> TYPE: DNA
<213> ORGANISM: Artificial Sequence
<220> FEATURE:
<223> OTHER INFORMATION: primer P20-R

<400> SEQUENCE: 41
cggcggacat gtttaagcgt aatctggaac atcgtatggg ta        42

<210> SEQ ID NO 42
<211> LENGTH: 45
<212> TYPE: DNA
<213> ORGANISM: Artificial Sequence
<220> FEATURE:
<223> OTHER INFORMATION: primer P21-F

<400> SEQUENCE: 42
tcggagtgca cgaagaaaat tatgagatta aataaattta ttggc        45

<210> SEQ ID NO 43
<211> LENGTH: 70
<212> TYPE: DNA
<213> ORGANISM: Artificial Sequence
<220> FEATURE:
<223> OTHER INFORMATION: primer P21-R

<400> SEQUENCE: 43
ccgggtgcac ttacgcataa tccggcacat catacggata actagaattt ttgaactgtt        60
tattttagc        70

<210> SEQ ID NO 44
<211> LENGTH: 40
<212> TYPE: DNA
<213> ORGANISM: Artificial Sequence
<220> FEATURE:
<223> OTHER INFORMATION: primer P22-F

<400> SEQUENCE: 44
tgaggaatgg gtccctatgc gatcgcaagg ccggcctatc        40

<210> SEQ ID NO 45
<211> LENGTH: 41
<212> TYPE: DNA
<213> ORGANISM: Artificial Sequence
<220> FEATURE:
<223> OTHER INFORMATION: primer P22-R

<400> SEQUENCE: 45
ttaagatagg ccggccttgc gatcgcatag ggacccattc c         41

<210> SEQ ID NO 46
<211> LENGTH: 64
<212> TYPE: DNA
<213> ORGANISM: Artificial Sequence
<220> FEATURE:
<223> OTHER INFORMATION: primer P23-F

<400> SEQUENCE: 46
gtcccctgat agctagctca gtcctaggga ttatgctagc tactagagat taaagaggag    60
aaac                                                                64

<210> SEQ ID NO 47
<211> LENGTH: 65
<212> TYPE: DNA
<213> ORGANISM: Artificial Sequence
<220> FEATURE:
<223> OTHER INFORMATION: primer P23-R

<400> SEQUENCE: 47
ttaagtttct cctctttaat ctctagtagc tagcataatc cctaggactg agctagctat    60
caggg                                                               65

<210> SEQ ID NO 48
<211> LENGTH: 65
<212> TYPE: DNA
<213> ORGANISM: Artificial Sequence
<220> FEATURE:
<223> OTHER INFORMATION: primer P24-F

<400> SEQUENCE: 48
gtcaagcagt tttggaaaag ttatcatcat tataaaggta aaacccatat gaatatcctc    60
cttag                                                               65

<210> SEQ ID NO 49
<211> LENGTH: 64
<212> TYPE: DNA
<213> ORGANISM: Artificial Sequence
<220> FEATURE:
<223> OTHER INFORMATION: primer P24-R

<400> SEQUENCE: 49
agataagaag tgagttttaa ctcacttctt aaacttgttt attcgtgtag gctggagctg    60
cttc                                                                64

<210> SEQ ID NO 50
<211> LENGTH: 97
<212> TYPE: DNA
<213> ORGANISM: Artificial Sequence
<220> FEATURE:
<223> OTHER INFORMATION: primer P25-F

<400> SEQUENCE: 50
atagtcagtt caaagttatc aatggcgaca atgtccatca gcagtatgtc gtcgatgcca    60
aaggagtctg gcgctgacat atgaatatcc tccttag                            97

<210> SEQ ID NO 51

```
<211> LENGTH: 93
<212> TYPE: DNA
<213> ORGANISM: Artificial Sequence
<220> FEATURE:
<223> OTHER INFORMATION: primer P25-R

<400> SEQUENCE: 51
tgaatgcttt gtgtaataaa aaagcagaca ggcgacggag tgaccactcc gtcgctttac      60
aaagagagga aaagtgtagg ctggagctgc ttc                                  93

<210> SEQ ID NO 52
<211> LENGTH: 67
<212> TYPE: DNA
<213> ORGANISM: Artificial Sequence
<220> FEATURE:
<223> OTHER INFORMATION: primer P26-F

<400> SEQUENCE: 52
cttcgtggtt atacttctgc taataatttt ctctgagagc atgcattcat atgaatatcc      60
tccttag                                                               67

<210> SEQ ID NO 53
<211> LENGTH: 72
<212> TYPE: DNA
<213> ORGANISM: Artificial Sequence
<220> FEATURE:
<223> OTHER INFORMATION: primer P26-R

<400> SEQUENCE: 53
gattctcttc gaataagcgg cgagcgcctt tgcgctcacc gcagcagtgt tggtgtaggc      60
tggagctgct tc                                                         72
```

PREVENTION OF STAPHYLOCOCCUS AUREUS INFECTIONS BY GLYCOPROTEIN VACCINES SYNTHESIZED IN ESCHERICHIA COLI

CROSS-REFERENCE TO RELATED APPLICATIONS

This application is filed pursuant to 35 U.S.C. § 371 as a United States National Phase Application of International Patent Application Serial No. PCT/EP2014/076468 filed Dec. 3, 2014, which claims priority to US Provisional No. 61/911,919 filed Dec. 4, 2013 and the entire contents of each of the foregoing applications are hereby incorporated by reference.

INTRODUCTION

Provided herein are immunogenic compositions and vaccines for the treatment and prevention of Staphylococcus aureus infections. These immunogenic compositions and vaccines comprise combinations of bioconjugates capsular polysaccharides that are N-linked to one or more carrier proteins.

BACKGROUND

Staphylococcus aureus is a major cause of invasive human infections, including bacteremia, endocarditis, pneumonia, and wound infections. Methicillin-resistant S. aureus (MRSA) are endemic in hospitals, and community-associated MRSA strains are spreading worldwide, posing a major global challenge [1-3]. There is an urgent need for a vaccine to prevent staphylococcal disease. Several vaccines have been tested in clinical trials, but capsular polysaccharide (CP) conjugates, individual protein antigens, and monoclonal antibodies (mAbs) to lipoteichoic acid have failed at various developmental stages, underscoring the need for novel vaccines with broader efficacy [4-6]. S. aureus vaccines that elicit both humoral and cell mediated immune responses are currently under evaluation [7], and both alpha toxin (Hla) and CPs are key antigens under consideration for inclusion in a multi73 component vaccine.

Serotype 5 (CP5) or serotype 8 (CP8) capsules are produced by ~75% of S. aureus clinical isolates, and CP antigens are critical for survival in the blood of infected animals [8, 9]. Capsular antibodies are opsonic, mediating uptake and killing of staphylococci by human neutrophils [8]. Hla is a secreted pore forming toxin to which lymphocytes, macrophages, alveolar epithelial cells, pulmonary endothelium, and erythrocytes are sensitive [10]. A genetically detoxified protein ($Hla_{H35L}$) is defective in pore formation, and antibodies to $Hla_{H35L}$ neutralize the lytic activity of native Hla [11]. Immunization with $Hla_{H35L}$ protects mice against lethal staphylococcal pneumonia, lethal peritonitis, and skin infections [12-14].

Immunization with conserved staphylococcal protein antigens glycosylated with CPs may be an elegant and efficient strategy to prevent S. aureus infections, limiting the numbers of individual vaccine components that need to be prepared and individually purified. Such an approach is feasible through the development of a novel Escherichia coli N-linked glycosylation technology [15, 16], wherein O antigens are transferred to specific sites within a protein carrier by the oligosaccharyltranferase PglB [15-17]. In contrast to chemically conjugated vaccines, bioconjugate vaccines are homogenous with a defined molecular structure, and the protein and glycan components are kept in native conformations, avoiding denaturation of essential B-cell epitopes [18]. The product contains peptide and covalently linked sugar epitopes from the same organism, thereby broadening its efficacy against numerous manifestations of microbial disease. We have prepared glycoconjugate vaccines comprised of CP5-Pseudomonas aeruginosa exoprotein A (Epa), CP8-Epa, and CP5-Hla and evaluated their protective efficacy against bacteremia and lethal pneumonia in mice. Whereas CP5-Epa and CP8-Epa significantly reduced bacteremia, the CP5-Hla bioconjugate vaccine protected against both bacteremia and lethal pneumonia.

BRIEF DESCRIPTION OF THE FIGURES

FIG. 1. Synthesis of the type 5 (CP5) and 8 capsular polysaccharides (CP8) of S. aureus in E. coli. A, Artificial gene clusters were constructed that encode enzymes responsible for the expression of CP5 or CP8 in E. coli. They comprise genes cloned from the S. aureus cap5 or cap8 locus (black) and the P. aeruginosa O11 LPS locus (gray). B, Biosynthesis of the CP5 or CP8 polymer showing enzymatic assembly, transport, and polymerization of the UDP-activated sugar precursors mediated by enzymes from S. aureus (black), P. aeruginosa (red) and E. coli (gray). The bolded enzymes were used to synthesize and assemble the CP5 and CP8 polymers in E. coli.

FIG. 3. S. aureus glycoconjugate vaccines were immunogenic in mice. Antigen-specific antibody levels in serum from mice immunized with PBS, Hla, or bioconjugate vaccine formulations were determined by ELISA at a 1:100 serum dilution. A, Antibody levels against CP5 in control mice or mice given increasing doses of biocojugate vaccines conjugated to Epa. B, Antibody levels to CP8 in mice immunized with CP8-Epa or 2a-Epa. C, Antibody levels to CP5 in control mice, mice given CP5-Hla, or Hla alone. D, Antibody levels to Hla in control mice, mice given CP5-Hla, or Hla alone. The ELISA index is calculated by dividing the OD at 405 nm of the test serum (diluted 1:100) by the OD at 405 nm of a control high-titered serum that is diluted and included on every assay.

FIG. 4. S. aureus glycoconjugate vaccines elicited functional antibodies. A, Rabbit IgG (10, 1, or 0.1 µg/ml) to either CP5-Epa or CP5-$Hla_{H35L}$ was opsonic for serotype 5 S. aureus strains Reynolds (CP5) and Newman in HL-60 opsonophagocytic killing (OPK) assays (n=3), whereas antibodies to Hla and *Shigella* O1-Epa were nonopsonic. B, OPK assays performed with human neutrophils revealed that rabbit antibodies to CP5-Epa were opsonic for Reynolds (CP5), C, Newman, D, USA100, and E, USA200 at concentrations as low a 1 µg/ml. Rabbit antibodies to the control bioconjugate *Shigella* O1-Epa vaccine lacked opsonic activity. OPK assays were performed as described (43) with CP5-Epa (concentrations shown are µg/ml), human polymorphonuclear leukocytes (PMNs), and guinea pig serum as a complement (C') source. F, Specificity of the assay was shown by the inability of CP5-Epa IgG to opsonize a serotype 8 strain (Reynolds [CP8] for phagocytic killing. The capsule negative Reynolds (CP−) strains was killed by PMNs+C' alone (with or without capsular antibodies). G, Rabbit IgG (≥1 µg/ml) to CP8-Epa was opsonic for serotype 8 *S. aureus* strains Reynolds (CP8) and MRSA strain ST80. No bacterial killing was observed in samples lacking antibodies or with *Shigella* 2a-Epa IgG. H, Sera from mice (n=7-16) immunized with 20 µg $Hla_{H135L}$ or 2 µg CP5-20 µg $Hla_{H135L}$ neutralized the lytic activity of Hla toward rabbit erythrocytes. Percent hemolysis was calculated compared to 100% lysis of erythrocytes with 4 U/ml of native Hla. Sera from mice immunized with $Hla_{H135L}$ showed greater in vitro neutralization activity than sera from mice given CP5-$Hla_{H135L}$. Lack of overlap in the 95% C.I. between the 50% lysis titers indicates differences significant at P<0.05; bars represent s.e.m.

FIG. 5. Active immunization with *S. aureus* glycoconjugate vaccines protects mice against bacteremia, weight loss, and renal abscesses. A, Mice immunized on days 0, 14, and 28 with CP5- Epa and challenged by the intraperitoneal route with ~$10^7$ CFU *S. aureus* Reynolds (CP5) had fewer bacteria recovered from the blood (P=0.0029) and B, kidneys (P<0.0001) and C, showed reduced weight loss (P=0.005) compared with mice immunized with *Shigella* O1-Epa. D, Mice immunized with 0.2 µg CP8-Epa and challenged with 3.9×$10^7$ CFU Reynolds (CP8) showed reduced bacteremia compared to control mice (P=0.0015). E, Mice immunized with 0.2 µg CP5-20 µg HlaH135L were protected against bacteremia and F, weight loss provoked by challenge with ~$10^7$ CFU strain Reynolds (CP5). Horizontal lines represent group medians. Statistical analysis was performed with a Mann-Whitney U test (*P<0.05, P<0.01 and *P<0.0001). G, Inverse correlation (P<0.001 by Spearman nonparametric analysis) between mouse CP5 antibody levels and bacteremia levels in mice actively immunized with CP5-$Hla_{H135L}$, 2a-Epa, or buffer. Mouse sera obtained one day prior to bacterial challenge were diluted 1:100 and tested by a CP5-specific ELISA. Mice were challenged intraperitoneally with 1×$10^7$ CFU of *S. aureus* Reynolds, and quantitative blood cultures were performed after 2 h. Each dot represents a sample from one mouse, and the lower limit of detection for bacteremia levels ranged from 5-20 CFU/ml.

FIG. 6. Immunization with CP5-$Hla_{H135L}$ protected mice against lethal pneumonia provoked by diverse *S. aureus* isolates. A, Mice immunized with 2 µg CP5-20 µg $Hla_{H135L}$ or 20 µg $Hla_{H135L}$ were protected from lethal pneumonia resulting from intranasal challenge with 1.4×$10^9$ CFU *S. aureus* Newman (n=15-18), B, 1.6×$10^9$ CFU LAC (n=8), or C, 6.0×$10^8$ CFU ST80 (n=9). D, Mice were immunized with bioconjugate vaccines on days 0, 14, and 28. Mice were injected with monoclonal antibodies to CD4 or CD8a 72 h and 24 h prior to challenge with *S. aureus* Newman. Control animals were given PBS. CP5-$Hla_{H135L}$ immunized mice (with or without T cell depletion) showed similar survival curves, whereas mice immunized with the *Shigella* 2a-EPA bioconjugate died within 24 h of bacterial challenge. Data were analyzed with the Log Rank test.

FIG. 7. Passive immunization with rabbit IgG specific for *S. aureus* bioconjugate vaccines protected mice against bacteremia and lethal pneumonia. A, Mice administered CP5-Epa IgG and challenged IP with 6×$10^6$ CFU *S. aureus* Reynolds (CP5) or B, 7×$10^7$ CFU USA200 had significantly fewer bacteria recovered from the blood 2 h post-challenge compared to mice given *Shigella* O1-Epa IgG. C, Mice given CP8-Epa IgG were protected against bacteremia induced by 4×$10^7$ CFU of *S. aureus* Reynolds (CP8). D, Mice administered CP5-Hla IgG showed reduced bacteremia provoked by *S. aureus* USA100 (8×107 CFU per mouse) or E, Newman (9×$10^7$ CFU/mouse). F, Mice passively immunized with 300 µg CP5-Epa or CP5-HlaH135L IgG showed similar reductions in bacteremia after challenge with strain Reynolds (CP5) (4×$10^6$ CFU). Antibodies to Hla had no effect on bacteremia levels. Horizontal lines represent group medians, and P values (*<0.05, <0.01 and *<0.0001) were determined with the Mann-Whitney U test. G, Mice (10/group) passively immunized with a single 1 mg dose of CP5-$Hla_{H135L}$ IgG or Hla IgG survived longer (P=0.0001) than mice given CP5-Epa IgG or O1-Epa IgG 24 h prior to intranasal challenge with 6.1×$10^8$ CFU *S. aureus* Newman. H, Mice given 1 mg of Hla IgG or CP5-$Hla_{H135L}$ IgG 4 h and 24 h prior to bacterial challenge with 9.7×$10^8$ CFU strain Newman were protected (P<0.0001) against lethal pneumonia. P values for the survival studies were determined with the Log Rank test.

FIG. 8. Sera from mice immunized with *S. aureus* bioconjugate vaccines mediated opsonophagocytic killing of staphylococci in an in vitro functional assay. (A) Sera (diluted three-fold from 1:50 to 1:109,350) pooled from mice immunized with CP5-Epa or CP5-$HlaH_{135}$ L were opsonic for serotype 5 *S. aureus* strains Reynolds (CP5) and Newman. (B) Sera (diluted three-fold from 1:50 to 1:109, 350) pooled from mice immunized with CP8-Epa was opsonic for serotype 8 strains Reynolds (CP8) and MRSA strain ST80. Samples lacking serum or containing pooled sera collected from mice prior to immunization (preimmune) or from mice immunized with *Shigella* 2a-Epa bioconjugate vaccine were poorly opsonic.

DETAILED DESCRIPTION

Figure 2C:
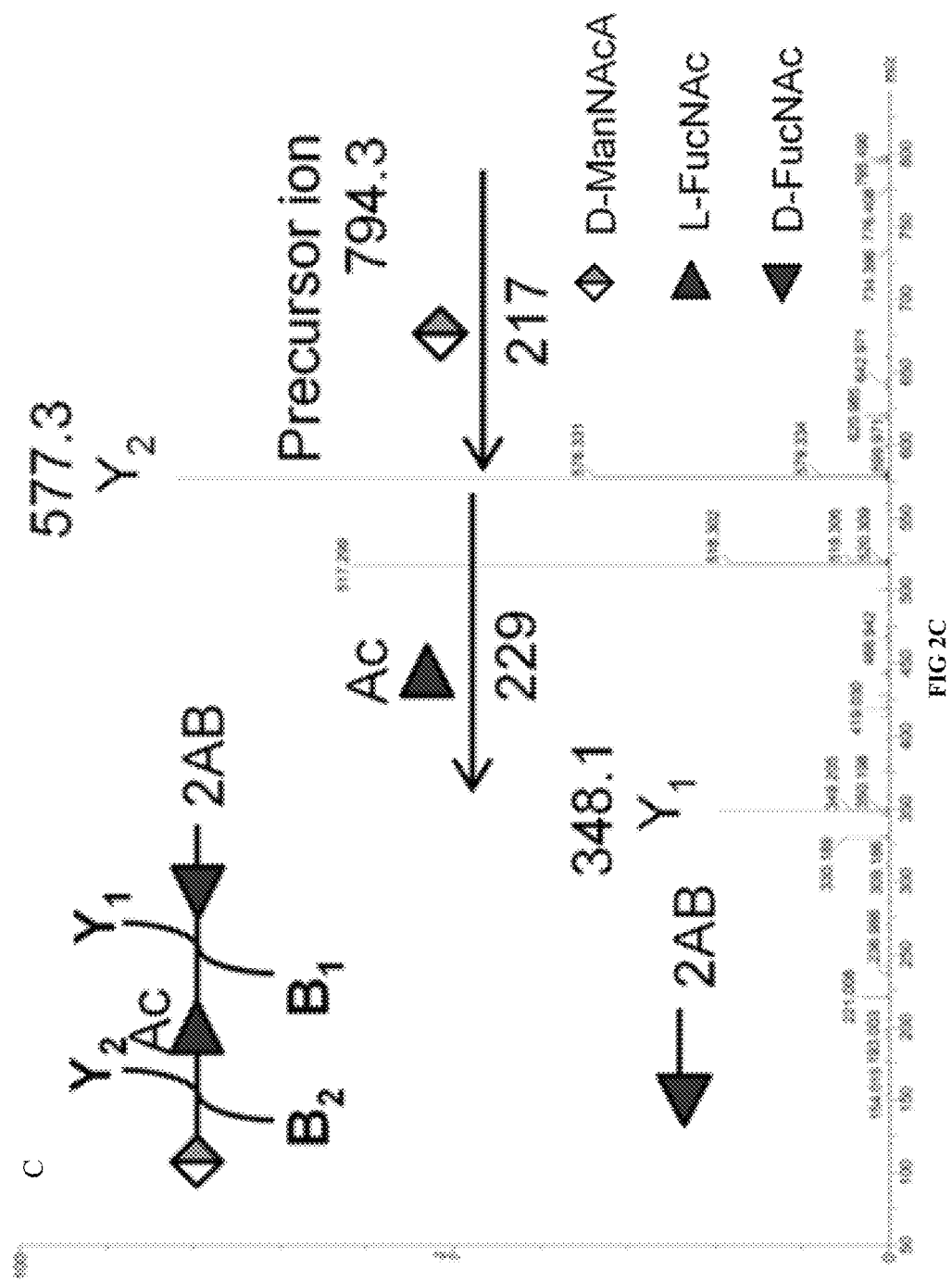
FIG. 2. Production of S. aureus type 5 (CP5) and 8 capsular polysaccharides (CP8) in E. coli. A, B, Structures of the S. aureus CP5 and CP8 repeating units are shown. Glycolipids were extracted from recombinant E. coli and labeled with 2-aminobenzamide (2-AB) after acid release from the lipid carrier; thus the reducing end of the CP5 and CP8 repeating subunits carries 2-AB. MALDI-TOF/TOF MS-MS analyses of the HPLC elution peaks with a mass-to-charge ratio of 794.3 were performed. The fragmentation patterns of C, CP5, and D, CP8 are shown with arrows pointing to the corresponding monosaccharides. Proteinase K-treated whole cell lysates from E. coli cells expressing S. aureus CPs were prepared and separated by SDS-PAGE. E, CP5, and F, CP8 polymers were visualized by silver staining and Western blots probed with antibodies to CP5 or CP8. Purified bioconjugates from E. coli expressing either G, CP5-Epa, H, CP8-Epa, or I, CP5-Hla were separated by SDS-PAGE and stained with Coomassie Blue (CB). After transfer to nitrocellulose, the bioconjugates were detected by their reactivity with serum antibodies to P. aeruginosa exoprotein A (Epa), CP5, CP8, or alpha toxin (Hla).

Provided herein are immunogenic composition and vaccines for the treatment and prevention of *Staphylococcus aureus* infections. These immunogenic compositions and vaccines comprise combinations of bioconjugates capsular polysaccharides that are N-linked to one or more carrier proteins.

Capsular polysaccharides can be synthesized in a prokaryotic host cell (e.g., in *Escherichia coli*) as described previously. See, e.g., International Patent Application No. PCT/EP2011/057111 filed on May 4, 2011 published as WO 2011/138361, which is incorporated herein in its entirety. These capsular polysaccharides can be N-linked to a carrier protein via an oligasaccharyltransferase (such as pglB from *Campylobacter jejuni*) as described in e.g., International Patent Application No. PCT/EP2011/057111 filed on May 4, 2011 published as WO 2011/138361, which is incorporated herein in its entirety.

In certain embodiments, the carrier protein is a protein that naturally comprises one or more N-glycosylation consensus sequences. In other embodiments, one or more N-glycosylation consensus sequences have been recombinantly introduced into the carrier protein. Any carrier protein suitable for use in the production of conjugate vaccines can be used herein. Exemplary carrier proteins include, without limitation, Exotoxin A of *P. aeruginosa* (EPA), CRM 197, Diphtheria toxoid, tetanus toxoid, detoxified hemolysin A of *S. aureus* (Hla, e.g., Hla H35L), clumping factor A of *S. aureus* (ClfA), clumping factor B of *S. aureus, E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *C. jejuni* AcrA, and *C. jejuni* natural glycoproteins, *S. pneumoniae* pneumolysin and additional *S. pneumoniae* protein antigens, e.g., *S. pneumoniae* NOX, *S. pneumoniae* PspA, *S. pneumoniae* PcpA, *S. pneumoniae* PhtD, *S. pneumoniae* PhtE, *S. pneumoniae* Ply, and *S. pneumoniae* LytB. In certain embodiments, the carrier protein is fused to a signal peptide such that the carrier protein is located into the periplasmic space of a Gram negative host cell (e.g., *E. coli*). In a specific embodiment, the signal peptide is the DsbA signal peptide.

In certain embodiments, a composition provided herein comprises (i) capsular polysaccharide type 8 that is N-linked to ClfA (CP8-ClfA); and (ii) a second capsular polysaccharide N-linked to a carrier protein. In more specific embodiments, the second capsular polysaccharide N-linked to a carrier protein is CP5-EPA, CP5-ClfA, CP5-Hla, CP8-EPA, or CP8-Hla.

In certain embodiments, a composition provided herein comprises (i) capsular polysaccharide type 5 that is N-linked to Hla (CP5-Hla); and (ii) a second capsular polysaccharide N-linked to a carrier protein. In more specific embodiments, the second capsular polysaccharide N-linked to a carrier protein is CP5-EPA, CP5-ClfA, CP8-EPA, CP8-ClfA, or CP8-Hla.

In certain embodiments, a composition provided herein comprises (i) capsular polysaccharide type 5 that is N-linked to Hla (CP5-Hla); (ii) capsular polysaccharide type 8 that is N-linked to ClfA (CP8-ClfA); and (iii) a third capsular polysaccharide N-linked to a carrier protein. In more specific embodiments, the third capsular polysaccharide N-linked to a carrier protein is CP5-EPA, CP5-ClfA, CP8-EPA, or CP8-Hla.

In certain embodiments, a composition provided herein comprises CP5 and CP8 N-linked to one carrier protein. In other embodiments, a composition provided herein comprises CP5 and CP8 N-linked to two or more carrier proteins.

In certain embodiments, a composition provided herein comprises CP5 and CP8 N-linked to one carrier protein, wherein the carrier protein is obtained from *Staphylococcus aureus*, such as Hla or Clfa. In other embodiments, a composition provided herein comprises CP5 and CP8 N-linked to two or more carrier proteins, wherein one, two, or all of these carrier proteins are obtained from *Staphylococcus aureus*, such as Hla or Clfa.

In another aspect, provided herein is a method of treating a subject (e.g., a human subject) having or at risk of developing a *Staphylococcus aureus* infection, wherein said method comprises administering to the subject one or more compositions described herein.

In a specific embodiment, provided herein is a method of treating a subject having or at risk of developing a *Staphylococcus aureus* infection, wherein said method comprises administering to the subject a composition comprising (i) a first bioconjugate comprising capsular polysaccharide type 8 that is N-linked to ClfA (CP8-ClfA); and (ii) a second bioconjugate comprising a second capsular polysaccharide N-linked to a carrier protein. In a specific embodiment, the second capsular polysaccharide N-linked to a carrier protein is CP5-EPA, CP5-ClfA, CP5-Hla, CP8-EPA, or CP8-Hla. In certain embodiments, the first and second bioconjugates are administered to the subject as part of the same composition. In certain embodiments, the first and second bioconjugates are administered to the subject as part of the same therapeutic regimen, but as different compositions.

In another specific embodiment, provided herein is a method of treating a subject having or at risk of developing a *Staphylococcus aureus* infection, wherein said method comprises administering to the subject a composition comprising (i) a first bioconjugate comprising capsular polysaccharide type 5 that is N-linked to Hla (CP5-Hla); and (ii) a second bioconjugate comprising a second capsular polysaccharide N-linked to a carrier protein. In a specific embodiment, the second capsular polysaccharide N-linked to a carrier protein is CP5-EPA, CP5-ClfA, CP8-EPA, CP8-ClfA, or CP8-Hla. In certain embodiments, the first and second bioconjugates are administered to the subject as part of the same composition. In certain embodiments, the first and second bioconjugates are administered to the subject as part of the same therapeutic regimen, but as different compositions.

In another specific embodiment, provided herein is a method of treating a subject having or at risk of developing a *Staphylococcus aureus* infection, wherein said method comprises administering to the subject a composition comprising (i) a first bioconjugate comprising capsular polysaccharide type 5 that is N-linked to Hla (CP5-Hla); (ii) a second bioconjugate comprising capsular polysaccharide type 8 that is N-linked to ClfA (CP8-ClfA); and (iii) a third bioconjugate comprising a third capsular polysaccharide N-linked to a carrier protein. In a specific embodiment, the third capsular polysaccharide N-linked to a carrier protein is CP5-EPA, CP5-ClfA, CP8-EPA, or CP8-Hla. In certain embodiments, the first, second, and/or third bioconjugates are administered to the subject as part of the same composition. In certain embodiments, the first, second, and/or third bioconjugates are administered to the subject as part of the same therapeutic regimen, but as different compositions.

In another specific embodiment, provided herein is a method of treating a subject having or at risk of developing a *Staphylococcus aureus* infection, wherein said method comprises administering to the subject a composition comprising CP5 and CP8 N-linked to one carrier protein. In another specific embodiment, provided herein is a method of treating a subject having or at risk of developing a *Staphylococcus aureus* infection, wherein said method comprises administering to the subject a composition comprising CP5 and CP8 N-linked to two or more carrier proteins. In certain embodiments, the carrier protein is a carrier protein obtained from *Staphylococcus aureus*, such as Hla or Clfa.

Articles of Manufacture

Also encompassed herein is a finished packaged and labeled pharmaceutical product. This article of manufacture includes the appropriate unit dosage form in an appropriate vessel or container such as a glass vial or other container that is hermetically sealed. The pharmaceutical product may contain, for example, one or more of the compositions described herein in a unit dosage form.

In a specific embodiment, the unit dosage form is suitable for parenteral, intravenous, intramuscular, intranasal, or subcutaneous delivery. Thus, encompassed herein are solutions, preferably sterile, suitable for each delivery route.

As with any pharmaceutical product, the packaging material and container are designed to protect the stability of the product during storage and shipment. Further, the products provided herein include instructions for use or other informational material that advise the physician, technician, or patient on how to appropriately prevent or treat an infection, e.g., a S. aureus infection. In other words, the article of manufacture includes instruction means indicating or suggesting a dosing regimen including, but not limited to, actual doses, monitoring procedures, and other information.

Specifically, provided herein is an article of manufacture comprising packaging material, such as a box, bottle, tube, vial, container, sprayer, insufflator, intravenous (i.v.) bag, envelope and the like; and at least one unit dosage form of a vaccine or composition (e.g., pharmaceutical composition) described herein contained within said packaging material, wherein said vaccine or composition (e.g., pharmaceutical composition) described herein comprises a S. aureus vaccine described herein, and wherein said packaging material includes instruction means which indicate that said composition described herein can be used to prevent, manage, and/or treat a S. aureus infection or one or more symptoms thereof by administering specific doses and using specific dosing regimens as described herein.

In a specific embodiment, an article of manufacture provided herein comprises a (i) a first bioconjugate comprising capsular polysaccharide type 8 that is N-linked to ClfA (CP8-ClfA); and (ii) a second bioconjugate comprising a second capsular polysaccharide N-linked to a carrier protein. In a specific embodiment, the second capsular polysaccharide N-linked to a carrier protein is CP5-EPA, CP5-ClfA, CP5-Hla, CP8-EPA, or CP8-Hla. In certain embodiments, the first and second bioconjugates are provided in the same composition. In certain embodiments, the first and second bioconjugates are provided in different compositions (e.g., in separate containers).

In another specific embodiment, an article of manufacture provided herein comprises a (i) a first bioconjugate comprising capsular polysaccharide type 5 that is N-linked to Hla (CP5-Hla); and (ii) a second bioconjugate comprising a second capsular polysaccharide N-linked to a carrier protein. In a specific embodiment, the second capsular polysaccharide N-linked to a carrier protein is CP5-EPA, CP5-ClfA, CP8-EPA, CP8-ClfA, or CP8-Hla. In certain embodiments, the first and second bioconjugates are provided in the same composition. In certain embodiments, the first and second bioconjugates are provided in different compositions (e.g., in separate containers).

In another specific embodiment, an article of manufacture provided herein comprises a (i) a first bioconjugate comprising capsular polysaccharide type 5 that is N-linked to Hla (CP5-Hla); (ii) a second bioconjugate comprising capsular polysaccharide type 8 that is N-linked to ClfA (CP8-ClfA); and (iii) a third bioconjugate comprising a third capsular polysaccharide N-linked to a carrier protein. In a specific embodiment, the third capsular polysaccharide N-linked to a carrier protein is CP5-EPA, CP5-ClfA, CP8-EPA, or CP8-Hla. In certain embodiments, the first, second, and/or third bioconjugates are provided in the same composition. In certain embodiments, the first, second, and/or third bioconjugates are provided in different compositions (e.g., in separate containers).

EXAMPLES

Expression of CP5 and CP8 in E. coli and Bioconjugate Vaccine Production

The bacterial strains, plasmid constructs, primers, and details of bioconjugate vaccine preparation are provided in the Supplemental Methods. Briefly, genes from the P. aeruginosa O11 O antigen gene cluster (wzz to wbpM) were amplified by PCR and cloned in a plasmid with S. aureus cap5HIJK or cap8HIJK. Recombinant plasmids were introduced into E. coli strains with mutations in lipopolysaccharide and enterobacterial antigen expression, resulting in expression of CP5 and CP8 in E. coli. Epa was modified for detoxification [19], replacement of the N-terminal signal peptide with the E. coli DsbA signal peptide, addition of two glycosylation consensus sequences [20], and insertion of a C terminal hexahistidine tag. An expression plasmid for recombinant expression of $Hla_{H35L}$ with one glycosite and a signal sequence for periplasmic localization was designed based on the published [11, 21] and detoxified version of S. aureus Hla.

Plasmids containing PglB and Epa or Hla were transformed into E. coli cells expressing CP5 or CP8. E. coli containing the recombinant plasmids were grown to logarithmic phase, and expression of PglB and either Epa or Hla was induced by addition of 1 mM IPTG and 0.2% arabinose. After overnight incubation at 37° C., the E. coli were harvested, and the bioconjugates were extracted by osmotic shock or high pressure homogenization [15, 16]. The bioconjugate vaccines were purified by immobilized metal affinity, anionic exchange, hydroxyapatite, and size exclusion chromatography as detailed in the Supporting Information.

Bacterial Cultures

S. aureus strains Reynolds (CP5), Reynolds (CP8), and Newman were described previously [9, 22]. S. aureus strains LAC and ST80 are community associated MRSA isolates [23, 24]. Strains NRS 382 (USA100) and NRS 383 (USA200) are hospital-associated MRSA strains obtained from the Network on Antimicrobial Resistance in Staphylococcus aureus program supported under NIAID NIH Contract No. HHSN272200700055C. For bacteremia studies and opsonophagocytic killing (OPK) assays, S. aureus strains were cultivated for 24 h at 37° C. on Columbia agar (Difco Laboratories) supplemented with 2% NaCl [9]. For pneumonia studies, staphylococci were harvested from tryptic soy broth (Difco) cultures grown to the logarithmic phase of growth, as described [25].

Opsonophagocytic Killing Assays

Human blood was collected from healthy volunteers giving written informed consent, as approved under institutional guidelines. The conventional OPK assay (0.5 ml volume) was performed with human neutrophils as described [26]. The microtiter-based OPK assay was based on that described by Burton and Nahm [27]. HL-60 cells (ATCC) were utilized at low passage (<3 mo) and maintained in L-glutamine-containing RPMI 1640 medium (Mediatech) supplemented with 10% heat-inactivated fetal bovine serum (HyClone), 100 U/ml penicillin, 100 μg/ml streptomycin, and 0.25 μg/ml amphotericin (Mediatech). The cells were differentiated to granulocytes with N, N-dimethylformamide as described [27], and their phenotype confirmed by flow cytometry [27]. The assay was performed in 96-well plates, and each well (80 μl) contained 4×10⁵ HL60 cells, 10³ CFU S. aureus, rabbit IgG or mouse serum, and 1% guinea pig serum (Cedarlane) as a complement (C') source. After a 2 h incubation at 37° C. with shaking, HL60 cells were lysed by the addition of 20 μl 1% Triton X-100. The samples were plated in duplicate, and the percent change in CFU/ml (i.e., killing) was defined as the reduction in CFU/ml after 2 h compared with that at time zero.

Hla Neutralization Assay

Hla (4 HU/ml; Toxin Technology) was incubated for 1 h with serial two-fold dilutions of serum from immunized mice. An equal volume of washed 2% rabbit erythrocytes was added and incubated for 60 min. The samples were centrifuged at 200×g for 10 min, and the OD545 nm of the supernatants was measured. The percent hemolysis of each sample was compared to erythrocytes lysed with 4 HU of Hla. The 50% inhibition titer was calculated using non-linear regression for sigmoidal curves with variable slopes (PRISM 4 software).

Animal Infection Studies

Animal studies were conducted according to institutional IACUC guidelines. Swiss-Webster mice (purchased from Taconic Farms or Charles River Laboratories) were immunized on days 0, 14, and 28 by the subcutaneous (SC) route. Control animals received an irrelevant Shigella O-antigen bioconjugate vaccine (O1-Epa or 2a-Epa). EPA-conjugates were formulated with Alhydrogel®, and CP5-Hla was formulated with Adju-Phos® to obtain a final Al3+concentration of 0.06%.

Mice were bled before each immunization and before bacterial challenge. Sera diluted 1:100 were tested by ELISA in microtiter plates coated with purified CPs (4 µg/ml) coupled to poly-L-lysine [28] or native Hla (1 µg/ml). Two weeks after the last immunization, mice were inoculated by the intraperitoneal (IP) route with S. aureus, and quantitative blood cultures were performed 2 h after challenge [9]. Weight loss and renal infection were evaluated on day 4, and culture data were analyzed by the Mann-Whitney U test. Mice were inoculated by the intranasal route for the lethal pneumonia model [25], and survival data were analyzed using the Log Rank test (Prism 4 software). For passive immunization against bacteremia, mice were given rabbit IgG (300 µg-1 mg) intravenously (IV) 24 h before challenge. Mice were bled for culture 1-2 h after bacterial challenge.

For passive immunization against lethal pneumonia, mice were injected IP with 1 mg rabbit IgG 24 h (or 24 h and 4 h) prior to bacterial inoculation. For T cell depletion studies, actively immunized mice were injected IP with either 500 µg rat anti-mouse CD4 (clone GK 1.5) or rat anti-mouse CD8a (clone 8 53-6.7) mAbs 72 h and 24 h prior to intranasal challenge with S. aureus Newman. Depletion of CD4+ or CP8+ cells was verified by flow cytometric analysis of splenic lymphocytes.

Results

Figure 2D:
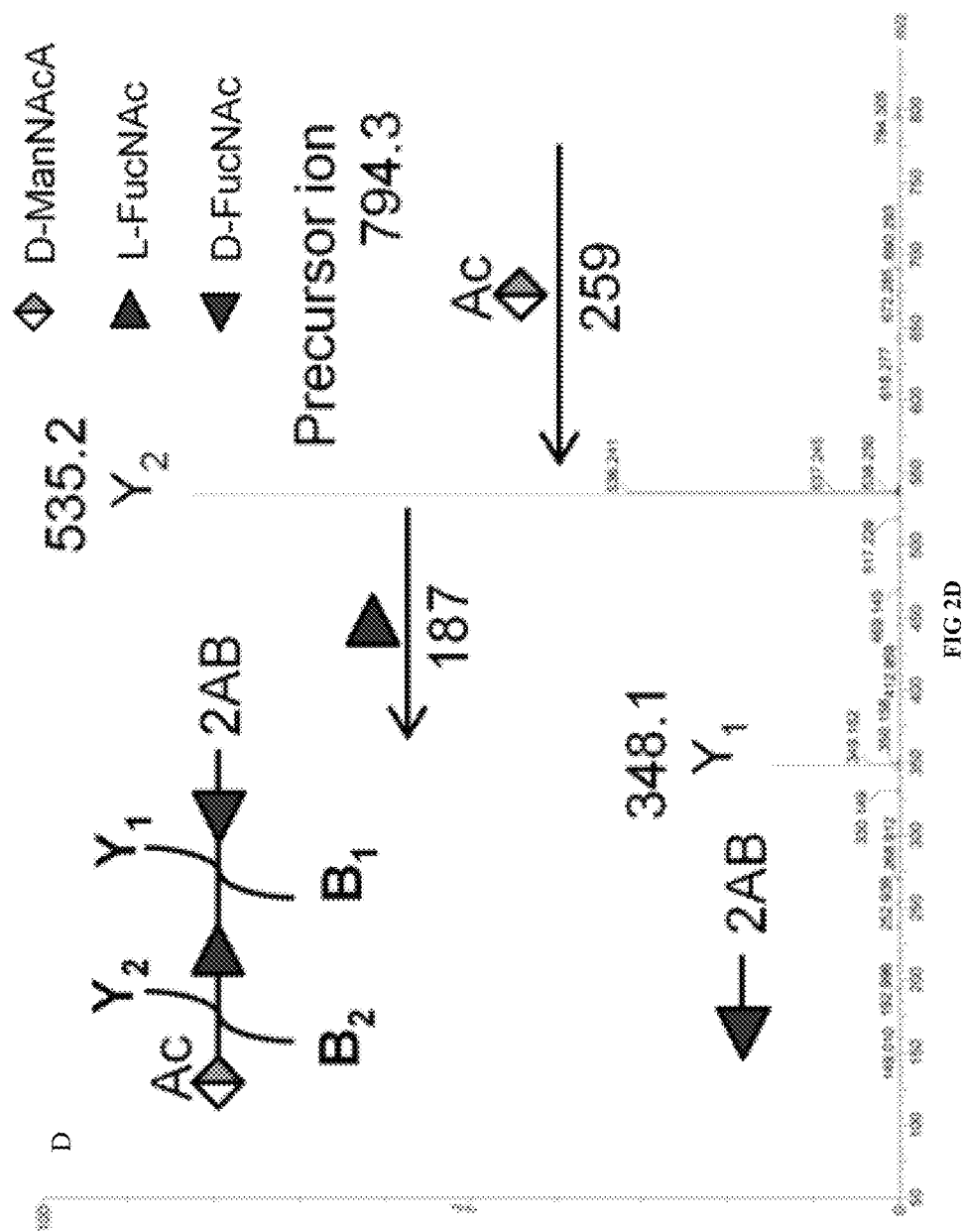

Synthesis of S. aureus CPs in E. coli The S. aureus CPs are assembled on the bacterial membrane carrier lipid undecaprenyl pyrophosphate by a conserved pathway that shares homology to the polymerase-dependent pathway of O polysaccharide synthesis in Gram-negative bacteria [29]. O antigen assembly is initiated by the transfer of a sugar phosphate from a UDP-donor to undecaprenyl phosphate. The lipid linked O antigen is assembled at the cytoplasmic side of the inner membrane by sequential action of different glycosyltransferases. The glycolipid is then flipped to the periplasmic space and polymerized. By replacing the O antigen ligase WaaL with the oligosaccharyltransferase PglB, the polymerized O antigen can be transferred to a protein carrier of choice rather than to the lipid A core [16] [30]. To synthesize S. aureus CP5 or CP8 in an E. coli strain deficient in O antigen production, we constructed plasmid-based chimeric genetic clusters containing genes with known function from S. aureus and P. aeruginosa (FIG. 1A). The gene clusters were designed based on the similar structures of S. aureus CPs and the P. aeruginosa O11 antigen, as each contains a FucNAc disaccharide as part of the trisaccharide repeating unit [31, 32]. In combination with E. coli monosaccharide biosynthesis genes, the enzymes encoded by these genes were predicted to synthesize an undecaprenyl pyrophosphate-linked CP5 or CP8 polymer consisting of repeating trisaccharide units (FIG. 1B). The recombinant plasmids were transformed into an E. coli strain with a deletion in the O-antigen ligase WaaL, and the bacterial glycolipids were extracted. The polysaccharides were released from the carrier lipid by mild acid treatment, labeled by 2-aminobenzamide (2-AB), and separated by HPLC. Single repeating subunits of CP5 (FIG. 2A) and CP8 (FIG. 2B) were collected and characterized using MALDI-Q TOF/TOF analysis. The major ion seen at a mass-to-charge ratio of 794.3 was subjected to MS-MS. The series of fragment ions were in agreement with the expected ions of the Na-adduct of the CP5 and CP8 single repeating units containing 2-AB at the reducing end (FIGS. 2, C and D). To show that the CP5 and CP8 subunits were polymerized and transferred to lipid A, proteinase K digests of whole cell extracts from E. coli cells expressing WaaL were prepared and separated by SDS-PAGE. Engineered E. coli cells synthesized a CP5 or CP8 polymer visualized by silver staining and recognized on Western blots probed with S. aureus CP5- or CP8-specific antiserum, respectively (FIGS. 2, E and F).

Enzymatic Synthesis of S. aureus Bioconjugate Vaccines in E. coli

To produce S. aureus vaccines in E. coli, the lipid-linked CPs were expressed in the presence of a protein carrier antigen and PglB. This allowed transfer of the polysaccharide from the carrier lipid to Asn residues within the consensus sequence D-X-N-X-S/T [20] of the protein antigen. E. coli cells expressing the CP5 or CP8 gene clusters, Epa containing two glycosylation consensus sequences, and PglB were cultivated. Expression of Epa and PglB was induced, and glycosylated Epa was extracted and purified. SDS-PAGE analysis revealed a ladder of bands between 90 and 170 kDa that reacted with antibodies to Epa and CP5 (FIG. 2G) or Epa and CP8 (FIG. 2H), indicating variable glycosylation of Epa with S. aureus CP antigens.

A second-generation vaccine system was designed to glycosylate a staphylococcal protein antigen (Hla) in E. coli. $Hla_{H35L}$ containing a glycosylation consensus sequence at amino acid 130 was constructed. E. coli cells carrying genes encoding CP5 biosynthesis, $Hla_{H35L}$, and PglB were cultivated. Expression of $Hla_{H35L}$ and PglB was induced, and CP5-$Hla_{H35L}$ was purified. The CP5-HlaH35L glycoconjugate subjected to SDS-PAGE revealed a ladder of bands between 55 and 70 kDa that reacted with antibodies to Hla and CP5 (FIG. 2I). This finding confirms that $Hla_{H35L}$ can be glycosylated with CP5.

Immunogenicity of Bioconjugate Vaccines in Mice

Mice were immunized with CP5-Epa, CP8-Epa or CP5-$Hla_{H35L}$. The CP5-Epa vaccine showed optimal immunogenicity at 0.2-1 µg CP5/mouse (FIG. 3A), and CP8-Epa showed good immunogenicity at 0.2 µg CP8 (FIG. 3B). CP5-$Hla_{H35L}$ was immunogenic at CP5 concentrations of 0.2 and 2 µg/mouse (FIG. 3C). Because the optimal $Hla_{H35L}$ dose was 20 µg/mouse (FIG. 3D), a 2 µg CP5-20 µg $Hla_{H35L}$ vaccine was chosen for further evaluation.

Bioconjugate Vaccines Elicit Functional Antibodies

In the presence of HL60 phagocytic cells and serum complement, rabbit IgG raised to CP5-Epa or CP5-$Hla_{H35L}$ was opsonic for CP5+ S. aureus strains Reynolds and Newman (FIG. 4A). IgG concentrations of ≥1 µg/ml resulted in >50% killing of the staphylococcal inoculum. Similarly, serum from mice immunized with CP5-Epa or CP5-Hla$_{H35L}$ showed OPK activity against CP5-producing *S. aureus* (Supplemental FIG. 1A). Rabbit antibodies to CP5-Epa were also opsonic for *S. aureus* strains Reynolds (CP5) and Newman when human neutrophils were included as the phagocytic cell source (FIGS. 4, B and C). MRSA strains USA100 and USA200 (both CP5+) were also killed in the presence of CP5-Epa antibodies, human neutrophils, and serum complement (FIGS. 4, D and E). CP5 antibodies were not opsonic for Reynolds (CP8). The Reynolds (CP−) strain was killed by neutrophils and complement without added antibodies (FIG. 4F). Rabbit CP8-Epa IgG was opsonic for *S. aureus* strains Reynolds (CP8) and MRSA strain ST80 (FIG. 4G) at concentrations ≥1 µg/ml. Likewise, mouse CP8-Epa antiserum showed good opsonic activity (Supplemental FIG. 1B) against CP8+ *S. aureus* strains.

Functional antibodies to Hla neutralize its lytic activity. As shown in FIG. 4H, mouse sera against either Hla$_{H35L}$ or CP5-Hla$_{H35L}$ neutralized the in vitro lytic activity of native Hla. Mice immunized with 20 µg Hla$_{H35L}$ showed higher neutralizing titers than mice given 2 µg CP5-20 µg Hla$_{H35L}$.

Bioconjugate Vaccines Protect Mice Against *S. aureus* Bacteremia

Mice immunized with CP5-Epa or the *Shigella* O1-Epa vaccine were challenged IP with *S. aureus* Reynolds (CP5). Mice given CP5-Epa were protected against bacteremia (FIG. 5A), renal abscess formation (FIG. 5B), and weight loss (FIG. 5C) compared to mice given the irrelevant *Shigella* vaccine. Similarly, animals immunized with CP8-Epa and challenged with Reynolds (CP8) showed a significant reduction in bacteremia (FIG. 5D).

The second-generation bioconjugate vaccine contained a staphylococcal toxoid (Hla$_{H35L}$) glycosylated with CP5. CP5-Hla$_{H35L}$ was protective against bacteremia (FIG. 5E) and associated weight loss (FIG. 5F) provoked by challenge with Reynolds (CP5). There was an inverse correlation between CP5 antibody levels and bacteremia levels in individual mice (FIG. 5G), confirming that protection was mediated by vaccine-induced antibodies.

CP5-Hla$_{H35L}$ Protects Against Lethal Pneumonia Caused By CP5+ and CP8+ *S. aureus*.

Mice were immunized with Hla$_{H35L}$, CP5-Hla$_{H35L}$, CP5-Epa, or *Shigella* 2a-Epa and challenged intranasally with CP5+ strain Newman. Mice immunized with Hla$_{H35L}$ or CP5-Hla$_{H35L}$ were protected against lethal pneumonia. CP5 antibodies did not mediate protection, since mice immunized with CP5-Epa succumbed to the infection like the mice given *Shigella* 2a-Epa (FIG. 6A). The Hla$_{H35L}$ and CP5-Hla$_{H35L}$ vaccines also protected against lethal pneumonia induced by the CP-strain USA300 LAC (FIG. 6B) and the CP8+ MRSA strain ST80 (FIG. 6C). Despite the fact that HlaH35L elicited a higher neutralizing antibody response to Hla than CP5-Hla$_{H35L}$ (FIG. 4H), protection against pneumonia elicited by the two vaccines was equivalent. Thus, CP5 glycosylation of *S. aureus* Hla broadened the protective effect of the bioconjugate vaccine, such that it protected mice against both bacteremia (FIG. 5E) and lethal pneumonia (FIG. 6, A-C).

T Cells are Not Critical for CP5-Hla$_{H35L}$-Mediated Protection Against Lethal Pneumonia.

Our passive immunization experiments (described below) and previous reports [13, 33] suggest that Hla antibodies alone are protective against *S. aureus* lethal pneumonia. To address a possible role for 12 T cells in immunity to staphylococcal pneumonia, we immunized mice with CP5-Hla$_{H35L}$ or *Shigella* 2a-Epa. The animals were given 500 µg rat anti-mouse CD4 (clone GK 1.5) or rat anti-mouse CD8a (clone 53-6.7) mAbs 72 h and 24 h prior to challenge with *S. aureus* Newman. Control mice were given PBS. Depletion of CD4+ or CP8+ cells was verified by flow cytometric analysis of splenocytes from treated animals. Control CP5-Hla$_{H35L}$ immunized mice and those subjected to T cell depletion showed similar survival in the lethal pneumonia model, whereas mice immunized with *Shigella* 2a-Epa succumbed to the infection (FIG. 6D). These results indicate that T cells are not critical for CP5-Hla$_{H35L}$-mediated protection against lethal *S. aureus* pneumonia.

Antibodies to Bioconjugate Vaccines Protected Against Bacteremia and Lethal Pneumonia One day before IP challenge with *S. aureus*, mice were passively immunized IV with rabbit IgG to CP5-Epa, CP8-Epa, or CP5-Hla$_{H35L}$. Compared to *Shigella* O1-Epa antibodies, CP5-Epa antibodies were protective against bacteremia induced by Reynolds (CP5) (FIG. 7A) and by MRSA strain USA200 (FIG. 7B). Similarly, Reynolds (CP8) bacteremia was significantly reduced by antibodies to CP8-Epa (FIG. 7C). Antibodies to CP5-Hla$_{H35L}$ reduced bacteremia induced by MRSA strain USA100

(FIG. 7D), Newman (FIG. 7E), and Reynolds (CP5) (FIG. 7F). The protection was CP-specific since antibodies to either CP5-Epa or CP5-Hla$_{H35L}$ reduced bacteremia, whereas antibodies to *S. aureus* Hla$_{H35L}$ or *Shigella* 2a-Epa provided no protection (FIG. 7F).

Passive immunization with CP5-Hla$_{H35L}$ IgG administered IP 24 h prior to intranasal bacterial challenge provided limited protection against lethal pneumonia (FIG. 7G) induced by strain Newman. However, when a second dose of IgG was given 4 h prior to bacterial inoculation, 90% of the mice given CP5-Hla$_{H35L}$ survived a lethal inoculum (FIG. 7H).

Discussion

The increasing prevalence of *S. aureus* in the hospital and community and its expanding resistance to antibiotics has emphasized the need for a preventative vaccine against this microbe. However, development of an effective staphylococcal vaccine has remained elusive. Active immunization with 13 single component vaccines based on CPs or *S. aureus* iron surface determinant B failed to protect patients from invasive disease in phase III clinical trials [6, 7, 34, 35]. Similarly, passive immunization strategies targeting clumping factor A or lipoteichoic acid did not prevent staphylococcal sepsis in premature neonates [7]. Current endeavors are focused on the preparation of vaccines that target multiple staphylococcal virulence factors. In addition to the importance of antibodies in mediating toxin neutralization and opsonophagocytic killing by neutrophils, T cell-based immunity has recently been shown in animal infection models to be critical for vaccine-mediated protection induced by certain protein antigens [7, 36-38].

Because opsonophagocytic killing by neutrophils is a key component for host clearance of *S. aureus*, we have targeted staphylococcal CPs, which elicit opsonic antibodies. Production of glycoconjugate vaccines is complex and expensive, requiring the preparation of recombinant proteins and extraction and purification of complex polysaccharides. Due to the nonspecific nature of chemical conjugations, chemically conjugated vaccines are heterogenous, variable from batch to batch, and often produced in low yield. Moreover, conventional conjugation of polysaccharides to protein antigens requires denaturing chemicals that may affect the protein carrier or certain labile polysaccharides, resulting in alteration of critical epitopes.

We have developed a novel technology that allows the conjugation of an *S. aureus* CP to a relevant *S. aureus* protein without the risk of protein denaturation. The *Campylobacter oligosaccharyl* transferase PglB is able to transfer an oligosaccharide to a specific protein consensus sequence [20], thereby allowing the production of glycoproteins in bacterial cells. This protein glycosylation system has been functionally transferred into *E. coli* [15]. Using this glycosylation machinery, a variety of polysaccharides can be transferred to recombinant proteins, allowing the production of bioconjugates that can be exploited as novel vaccines. Bioconjugate vaccine lots are homogenous, and no free polysaccharide is present during the production to inhibit T-cell dependent immune responses. Because the bioconjugate is produced in *E. coli*, growth of toxic organisms for polysaccharide extraction is not required.

In this study we demonstrated production, purification, and efficacy of CP5-Epa and CP8-Epa bioconjugate vaccines. In addition, we showed that the disaccharide intermediate of *P. aeruginosa* O11 antigen can serve as substrate for *S. aureus* glycosyltransferases, showing for the first time that glycosyltransferases of Gram-positive and Gram-negative bacteria can be combined. The bioconjugate vaccines elicited opsonic antibodies in mice and rabbits, and active and passive immunization strategies protected mice against experimental bacteremia. The second-generation bioconjugate vaccine (CP5-Hla$_{H35L}$) was an important proof-of-concept product to show the potential of covalently linking protein and polysaccharide antigens from the same microbe. Like animals given CP5-Epa, mice immunized with CP5-Hla$_{H35L}$ were protected against bacteremia provoked by several CP5+ *S. aureus* isolates. Importantly, the CP5-Hla$_{H35L}$ vaccine also protected mice against lethal pneumonia induced by serotype 5, serotype 8, or capsule-negative *S. aureus* strains. Thus, the CP5-Hla$_{H35L}$ bioconjugate vaccine showed protective efficacy against bacteremia (mediated by CP5 antibodies) and lethal pneumonia (mediated by Hla$_{H35L}$ antibodies).

This novel glyco-engineering approach to conjugate vaccine development could revolutionize the industry. The trivalent *S. aureus* vaccine candidate (described herein) comprising CP5, CP8, and Hla$_{H35L}$ elicits functional antibodies and broadly protects in different animal models. Glycosylation of an *S. aureus* surface protein with CP8 has been accomplished, and it is currently undergoing production and testing. Glycoengineering technology enables the development of well-defined, novel and effective vaccines against microbial pathogens like *S. aureus*, for which protein or polysaccharide antigens alone are not sufficient to provide broad protection. In addition, conjugation of capsular antigens to protein antigens allows the reduction of components to be injected compared to a vaccine that contains separate capsular conjugate and protein components.

References

1. Bassetti M, Nicco E, Mikulska M. Why is community-associated MRSA spreading across the world and how will it change clinical practice? Int J Antimicrob Agents 2009; 34 Suppl 1:S15-9.
2. Bradley S F. *Staphylococcus aureus* pneumonia: emergence of MRSA in the community. Semin Respir Crit Care Med 2005; 26:643-9.
3. Chambers H F. Community-associated MRSA-resistance and virulence converge. N Engl J Med 2005; 352:1485-7.
4. Shinefield H, Black S, Fattom A, et al. Use of a *Staphylococcus aureus* conjugate vaccine in patients receiving hemodialysis. N Engl J Med 2002; 346:491-6.
5. Broughan J, Anderson R, Anderson A S. Strategies for and advances in the development of *Staphylococcus aureus* prophylactic vaccines. Expert Rev Vaccines 2011; 10:695-708.
6. Fowler V G, Allen K B, Moreira E D, et al. Effect of an investigational vaccine for preventing *Staphylococcus aureus* infections after cardiothoracic surgery: a randomized trial. JAMA 2013; 309:1368-78.
7. Proctor R A. Challenges for a universal *Staphylococcus aureus* vaccine. Clin Infect Dis 2012; 54:1179-86.
8. Thakker M, Park J-S, Carey V, Lee J C. *Staphylococcus aureus* serotype 5 capsular polysaccharide is antiphagocytic and enhances bacterial virulence in a murine bacteremia model. Infect Immun 1998; 66:5183-9.
9. Watts A, Ke D, Wang Q, Pillay A, Nicholson-Weller A, Lee J C. *Staphylococcus aureus* strains that express serotype 5 or serotype 8 capsular polysaccharides differ in virulence. Infect Immun 2005; 73:3502-11.
10. Bhakdi S, Tranum-Jensen J. Alpha-toxin of *Staphylococcus aureus*. Microbiol Rev 1991; 55:733-51.
11. Menzies B E, Kernodle D S. Site-directed mutagenesis of the alpha-toxin gene of *Staphylococcus aureus*: role of histidines in toxin activity in vitro and in a murine model. Infect Immun 1994; 62:1843-7.
12. Kennedy A D, Bubeck Wardenburg J, Gardner D J, et al. Targeting of alpha-hemolysin by active or passive immunization decreases severity of USA300 skin infection in a mouse model. J Infect Dis 2010; 202:1050-8.
13. Wardenburg J B, Schneewind O. Vaccine protection against *Staphylococcus aureus* pneumonia. J Exp Med 2008; 205:287-94.
14. Rauch S, DeDent A C, Kim H K, Bubeck Wardenburg J, Missiakas D M, Schneewind O. Abscess formation and alpha-hemolysin induced toxicity in a mouse model of *Staphylococcus aureus* peritoneal infection. Infect Immun 2012; 80:3721-32.
15. Wacker M, Linton D, Hitchen P G, et al. N-linked glycosylation in *Campylobacter jejuni* and its functional transfer into *E. coli*. Science 2002; 298:1790-3.
16. Feldman M F, Wacker M, Hernandez M, et al. Engineering N-linked protein glycosylation with diverse O antigen lipopolysaccharide structures in *Escherichia coli*. Proc Natl Acad Sci U S A 2005; 102:3016-21.
17. Wetter M, Kowarik M, Steffen M, Carranza P, Corradin G, Wacker M. Engineering, conjugation, and immunogenicity assessment of *Escherichia coli* O121 O antigen for its potential use as a typhoid vaccine component. Glycoconj J 2013; 30:511-22.
18. Ihssen J, Kowarik M, Dilettoso S, Tanner C, Wacker M, Thony-Meyer L. Production of glycoprotein vaccines in *Escherichia coli*. Microb Cell Fact 2010; 9:61.
19. Killeen K P, Collier R J. Conformational integrity of a recombinant toxoid of *Pseudomonas aeruginosa* exotoxin A containing a deletion of glutamic acid-553. Biochim Biophys Acta 1992; 1138:162-6.
20. Kowarik M, Young N M, Numao S, et al. Definition of the bacterial N-glycosylation site consensus sequence. EMBO J 2006; 25:1957-66.
21. Jursch R, Hildebrand A, Hobom G, et al. Histidine residues near the N terminus of staphylococcal alpha-toxin as reporters of regions that are critical for oligomerization and pore formation. Infect Immun 1994; 62:2249-56.
22. Duthie E S, Lorenz L L. Staphylococcal coagulase; mode of action and antigenicity. J Gen Microbiol 1952; 6:95-107.

23. Linde H, Wagenlehner F, Strommenger B, et al. Healthcare-associated outbreaks and community acquired infections due to MRSA carrying the Panton-Valentine leucocidin gene in southeastern Germany. Eur J Clin Microbiol Infect Dis 2005; 24:419-22.

24. Voyich J M, Otto M, Mathema B, et al. Is Panton-Valentine leukocidin the major virulence determinant in community-associated methicillin-resistant *Staphylococcus aureus* disease? J Infect Dis 2006; 194:1761-70.

25. Bubeck Wardenburg J, Palazzolo-Ballance A M, Otto M, Schneewind O, DeLeo F R.
Panton-Valentine leukocidin is not a virulence determinant in murine models of community-associated methicillin-resistant *Staphylococcus aureus* disease. J Infect Dis 2008; 198:1166-70.

26. Park S, Kelley K A, Vinogradov E, et al. Characterization of the structure and biological functions of a capsular polysaccharide produced by *Staphylococcus saprophyticus*. J Bacteriol 2010; 192:4618-26.

27. Burton R L, Nahm M H. Development of a fourfold multiplexed opsonophagocytosis assay for pneumococcal antibodies against additional serotypes and discovery of serological subtypes in Streptococcus pneumoniae serotype 20. Clin Vaccine Immunol 2012; 19:835-41.

28. Gray B M. ELISA methodology for polysaccharide antigens: protein coupling of polysaccharides for adsorption to plastic tubes. J Immunol 1979; 28:187-92.

29. Bugg T D, Brandish P E. From peptidoglycan to glycoproteins: common features of lipid-linked oligosaccharide biosynthesis. FEMS Microbiol Lett 1994; 119:255-62.

30. Wacker M, Casimiro D R. Synthesizing vaccines with microbes. In: von Gabain A, Klade C, eds. Development of Novel Vaccines. Wien: Springer-Verlag, 2012:125-45.

31. Dean C R, Franklund C V, Retief J D, et al. Characterization of the serogroup O11 O-antigen locus of *Pseudomonas aeruginosa* PA103. J Bacteriol 1999; 181: 4275-84.

32. Jones C. Revised structures for the capsular polysaccharides from *Staphylococcus aureus* types 5 and 8, components of novel glycoconjugate vaccines. Carbohydr Res 2005; 340:1097-106.

33. Ragle B E, Bubeck Wardenburg J. Anti-alpha-hemolysin monoclonal antibodies mediate protection against *Staphylococcus aureus* pneumonia. Infect Immun 2009; 77:2712-8.

34. Daum R S, Spellberg B. Progress toward a *Staphylococcus aureus* vaccine. Clin Infect Dis 2012; 54:560-7.

35. Schaffer A C, Lee J C. Staphylococcal vaccines and immunotherapies. Infect Dis Clin North Am 2009; 23:153-71.

36. Lin L, Ibrahim A S, Xu X, et al. Th1-Th17 cells mediate protective adaptive immunity against *Staphylococcus aureus* and *Candida albicans* infection in mice. PLoS Pathog 2009; 5:e1000703.

37. Joshi A, Pancari G, Cope L, et al. Immunization with *Staphylococcus aureus* iron regulated surface determinant B (IsdB) confers protection via Th17/IL17 pathway in a murine sepsis model. Hum Vaccin Immunother 2012; 8:336-46.

38. Narita K, Hu D L, Mori F, Wakabayashi K, Iwakura Y, Nakane A. Role of interleukin-17A in cell440 mediated protection against *Staphylococcus aureus* infection in mice immunized with the fibrinogen-binding domain of clumping factor A. Infect Immun 2010; 78:4234-42.

Supplemental Methods

Plasmids Expressing Epa, Hla$_{H35L}$, CP5, and PglB

Bacterial strains and plasmid constructs used for the preparation of bioconjugate vaccines are described in Table S1. *Pseudomonas aeruginosa* Epa was the carrier protein initially used for bioconjugate vaccine production. Epa was modified for detoxification [1], replacement of the N-terminal signal peptide with the *Escherichia coli* DsbA signal peptide, addition of two glycosylation consensus sequences [2], and insertion of a C terminal hexahistidine tag as follows.

An insert containing the *E. coli* signal sequence, an HA tag, and the mature bovine ribonuclease B was prepared by PCR using oligonucleotides P1-F/R (Table S2 lists all primers) and pSVSPORT/RNAse as template DNA [3]. The amplicon was treated with VspI and EcoRI and cloned into pEC415, resulting in pMIK11. The HA RNase segment was removed from the plasmid by NdeI and EcoRI digestion for replacement by an insert encoding the mature exoprotein A sequence (toxA) from *P. aeruginosa* strain DSM1117 with a C terminally fused hexahistidine tag. toxA was amplified by PCR using oligonucleotides P2-F/R, digested with NheI and EcoRI, and ligated into pMIK11. The resulting amino acid sequence at the N terminus was MKKIWLALAGLVLAF-SASAAEEA (SEQ ID NO:1). A QuikChange Site-Directed Mutagenesis kit (Stratagene) was used to introduce the detoxifying mutation L552V, ΔE553 into toxA using oligonucleotides P3-F/R. Further QuikChange mutagenesis was performed on the resulting plasmid (p70) to introduce a SmaI site around amino acid A376 of toxA using oligonucleotides P4-F/R, resulting in p88. To introduce a glycosylation site, p88 was digested using SmaI, and a cassette composed of two annealed complementary, phosphorylated oligonucleotides (P5-F/R) was ligated into the cut vector, resulting in p137. An additional glycosylation site was inserted into p137 to generate p150 by QuikChange mutagenesis using oligonucleotides P6-F/R.

An expression plasmid for recombinant expression of Hla$_{H35L}$ with one glycosite was designed based on the published [4, 5] and detoxified version of *Staphylococcus aureus* Hla. Specifically, the coding sequence for the signal sequence of *E. coli* DsbA was fused upstream and in frame with the coding sequence of the mature Hla$_{H35L}$ protein, followed by a downstream hexahistidine tag. Based on the published structure of Hla [6], a site for glycosylation was introduced by rational design at amino acid 130 of the fused sequence. The DNA encoding the mature, signal peptide cleaved Hla$_{H35L}$ with a glycosylation site and a hexahistidine tag was synthesized by a commercial provider and subcloned into the NheI and SalI sites in p150, resulting in plasmid p570.

To generate a plasmid for the recombinant expression of the biosynthetic pathway genes of *S. aureus* CPS in *E. coli*, a multiple cloning site (MCS) was inserted into the EcoRI site of pLAFR1 [7] using oligocassettes P7-F/R, resulting in plasmid p336. The *P. aeruginosa* O11 O antigen gene cluster (wzz to wbpM) was amplified from genomic DNA of *P. aeruginosa* strain PA103 by PCR using the oligos P8-F/R and cloned into the pLAFR1 MCS via Bsu36I and PciI, resulting in plasmid p341. *S. aureus* cap5H was subcloned with an HA tag, cap5I was subcloned with a myc tag, and cap5J was subcloned with a FLAG tag into pACT3 (cap5H-HA) and pEXT22 (cap5I-myc/cap5J-FLAG) [8]. We amplified the cap5 genes by PCR from genomic DNA of *S. aureus* Mu50 using the following primers: (i) cap5H-HA:P9-F/R, (ii) cap5I-myc: P10-F/R, (iii) cap5J-FLAG:P11-F/R. Within p341 the O11-wbjA-wzy genes were replaced with the *S.* aureus cap5HIJ genes using the method of Datsenko & Wanner [9]. The cap5H-HA-cap5I-myc-cap5J-FLAG fragment was jointly amplified in a first step by overlap-PCR using pACT3-cap5-HA and pEXT22-cap5I-myc-cap5J-FLAG as templates and the following primers for (i) PCR1 (cap5H-HA amplification): P12-F/R, (ii) PCR2 (cap5I-myc-cap5J-FLAG amplification): P13-F/R, (iii) overlap-PCR3 (joining cap5H-HA with cap5I-myc-cap5J-FLAG): P14-F/R. In a second overlap PCR the joined cap5H-HA-capI-myc-capJ-FLAG genes were fused to a selection marker (cat), flanked by FLP recognition target (FRT) sites using the PCR product from overlap PCR3 and pKD3 [9] as PCR templates, respectively, and the following primers for (i) PCR4 (amplification of FRT-flanked cat gene): P15-F/R, (ii) overlap-PCR5 (joining cap5H-HA-capI-myc-capJ-FLAG with cat gene): P16-F/R. The resultant PCR product was transformed into DH5α bacteria containing pKD46 [9] and p341, and chloramphenicol-resistant colonies were selected as described [9], generating p345. The gene cap5K encoding the CP5-specific flippase was amplified by PCR from genomic DNA of S. aureus Mu50 using the primers P17-F/R, thereby introducing an HA-tag. The amplicon was subcloned via MssI and Alw44I downstream of cap5J-FLAG into p345, resulting in plasmid p393.

To combine the genes encoding the expression of CP5 and PglB in one plasmid, the gene for HA-tagged pglB was combined with a constitutive promoter derived from the O-antigen gene cluster from E. coli O121 by means of overlap PCR and cloned into p393. The O121 rfb promotor region was amplified in the first PCR with the oligonucleotide pair P18-F/R using p331 containing the O121 O antigen cluster from E. coli O121 as template [10]. The gene for the HA tagged pglB was amplified in the second PCR with the oligonucleotide-pair P19-F/R using the PglB expression plasmid p114 [11] as template. The third overlap PCR was used to amplify and combine the O121 promoter region with the pglB gene into one PCR product by using the oligonucleotides P20-F/R and the PCR products from the first and second PCRs as templates. The overlap PCR product (O121-pglB)was cloned via the PscI restriction site into p393, resulting in plasmid p484.

To generate a plasmid for the recombinant expression of the biosynthetic pathway genes of S. aureus CP8 in E. coli, the cap5HIJ-cluster as present in the above described plasmid p345 was replaced by the cap8HIJ-cluster (originating from p327, see below) using the restriction endonucleases BspTI and Alw44I, resulting in plasmid p405. This cap8HIJ gene-cluster had been synthesized as codon-usage optimized ORF encoding also a Myc-tag (cap8H), a FLAG-tag (cap8I) and a HA-tag (cap8J) by GenScript Inc. and cloned into pUC57, resulting in plasmid p327. In addition the cap8HIJK genes were amplified using genomic DNA from the S. aureus strain MW2 and were subcloned into p345 using BspTI and Alw44I, thereby replacing cap5HIJ by cap8HIJK and resulting in the plasmid p404. This plasmid served as template in a PCR to amplify cap8K using the oligonucleotide pair P21-F/R introducing two Alw44I-sites (5' and 3') and the ORF for a HA-tag (3'). The PCR product was cloned unforced via Alw44I into p405 leading to p413. Within this plasmid the genes for O11 wzz-wzx were replaced by a MCS. For this purpose, the oligonucleotide pair P22-F/R was annealed and ligated via Eco81I and BspTI into the p413 plasmid, leading to the plasmid p555. A constitutive active promoter that was obtained by annealing the oligonucleotides P23 -F/R was cloned into the plasmid p555 via SanDI and BspTI, resulting in the plasmid p564.

Construction of E. coli Strains

Strain StGVXN1690 was constructed by the method of Datsenko and Wanner [9] for production of CP5-Epa and CP8-Epa. First, the waaL gene of E. coli W3110 was replaced by a cat resistance cassette to abrogate LPS synthesis. Oligonucleotides P24-F/R were used for PCR of the cat cassette using pKD3 as a template. The PCR product encoded the cat expression cassette flanked by FRT sites. After deletion of the waaL and insertion of the cat cassette, absence of waaL was evaluated by colony PCR. In addition, inability to produce LPS was analyzed by silver stain to confirm the knock out. The cat cassette was removed by site-specific FLP driven recombination as described [9] to introduce additional chromosomal mutations. To prevent synthesis of the enterobacterial common antigen (ECA), the stretch of genes from rmlB to wecG in the gene cluster was deleted using a PCR product generated from pKD3 and oligonucleotides P25-F/R. Mutagenesis was confirmed by i) sequencing of PCR products generated from the mutants and primers flanking the mutated DNA regions, ii) confirming the absence of LPS formation using silver staining, and iii) showing absence of ECA in immunoblots from proteinase K treated cell extracts and a monoclonal antibody for ECA detection [12].

E. coli strain StGVXN1717 was prepared by methods similar to those used to create strain StGVXN1690. The waaL gene was deleted and the cat cassette removed, then the wecA and wzzE genes from the ECA cluster were deleted using a PCR generated cat cassette from pKD3 and oligonucleotides P26-F/R. After removal of cat by site-specific FRT recombination, the rmlB-wecG DNA fragment was replaced chromosomally by another cat cassette as above.

Analysis of Undecaprenyl Pyrophosphate (Und-PP)-Linked CP5 and CP8 Glycans

The O antigen glycans were analyzed in E. coli strain StGVXN1690. CP5 was expressed by transforming cells with p393, and and CP8 was expressed by transforming the cells with p564. The strains were grown overnight in a shake flask. Cells equivalent to an $A_{600\ nm}$ of 400 were harvested, washed once with 0.9% NaCl, and lyophilized. CP5 and CP8 were extracted and analysed as described [10].

Production of Bioconjugate Vaccines

A 15-L bioreactor (New MBR AG) containing 7 L of batch medium (yeast extract [BD] 10 g/L, soy peptone [Organotechnie] 20 g/L, glycerol 53 g/L, 56 mM phosphate, 5 mM citrate, 2 mM $MgCl_2$, and trace elements) was inoculated to an $OD_{600\ nm}$ of 0.05 with E. coli strain StGVXN1690 p150, p114 and p393 for producing CP5-EPA or E. coli strain StGVXN1717 p570 and p484 for producing CP5-Hla$_{H35L}$. The cultures were grown at 37° C. under aerobic conditions. At an $OD_{600\ nm}$ of 40, the bacterial cells were induced with 1 mM IPTG (for production of CP5-EPA only) and 0.2% arabinose. Following induction, a constant feed (180 g/L glycerol, 100 g/L soy peptone, 33 mM $MgSO_4$, 1 mM IPTG and trace elements) was started with a flow rate of 186 g/h. At 15 h post induction, bacterial cells were harvested by centrifugation, washed with 0.9% NaCl and suspended to an $OD_{600\ nm}$ of 200 in immobilized metal affinity chromatography (IMAC) binding buffer (30 mM Tris, 500 mM NaCl, pH 8). The bacteria were homogenized in an APV1000 (APV Manufacturing) at 800 bar, followed by centrifugation to obtain the clarified homogenate as supernatant.

For production of CP8-Epa, Terrific broth supplemented with 10 mM $MgCl_2$ was inoculated with an overnight culture of E. coli (StGVXN1690 p150, p114 and p564) and incubated with shaking at 37° C. Cultures were induced at OD$_{600\,nm}$ of 0.9 with 1 mM IPTG and 0.1% arabinose, and the biomass was harvested the following day. The bacterial cells were washed with 0.9% NaCl and suspended to an OD$_{600\,nm}$ of 20 in lysis buffer (30 mM Tris HCl pH8.5, 1 mM EDTA, 20% sucrose). After incubation with stirring at 4° C. for 30 min in 1 mg/ml lysozyme (Sigma-Aldrich), the sample was centrifuged to obtain the soluble periplasmic extract.

Purification of Bioconjugate Vaccines

CP5-EPA was purified with three chromatography steps, starting with IMAC, followed by anion exchange, and finally size exclusion chromatography (SEC) as follows: 60 mL Ni-sepharose beads (GE-Healthcare) were added to the clarified homogenate. The beads with the bound glycoprotein were washed with IMAC binding buffer and packed into a chromatography column. The packed column was washed with 6 column volumes (CV) of IMAC-Buffer A (30 mM Tris, 200 mM NaCl, 10 mM imidazole, pH 8), followed by elution with 15 CV of a linear gradient from 0% to 100% IMAC-Buffer B (30 mM Tris, 200 mM NaCl, 500 mM imidazole, pH 8). Fractions were analyzed by SDS-PAGE, and those containing the glycoprotein were pooled and diluted with Q-Buffer A (10 mM Tris, pH 7) to 6.5 mS/cm conductivity. The diluted sample was loaded onto a 60 mL Q Ceramic HyperD F (Pall AG) chromatography column, washed with 4 CV Q-Buffer A, and eluted with a 15 CV linear gradient from 0 to 100% Q-Buffer B (10 mM Bis-Tris, 500 mM NaCl, pH 7). Fractions were analyzed by SDS-PAGE, and those containing the glycoprotein were pooled. The sample was concentrated to 25 mL by tangential flow filtration with a 10-kDa cut-off 115 cm$^2$ mPES hollow fiber (Spectrum Europe B.V.). Aliquots of 12.5 mL of the concentrated sample were loaded onto a XK26/60 column (GE Healthcare) packed with 320 mL Superdex 200 (GE Healthcare). Fractions resulting from isocratic elution with 1× PBS (Amresco) were analyzed by SDS-PAGE, and those containing the glycoprotein were pooled and stored at −80° C.

CP5-Hla$_{H35L}$ was purified via four sequential purification steps starting with IMAC and finishing with SEC as described for CP5-EPA. The intermediate purification steps, anion exchange followed by hydroxyapatite chromatography were performed as follows. The pooled fractions obtained from the IMAC were diluted with ANX-Buffer A (10 mM Tris pH 7.5) to 3 mS/cm conductivity and loaded onto a 16 mL bed volume ANX Sepharose 4 Fast Flow (High Sub) (GE Healthcare) column. The column was washed with 5 CV ANX-Buffer A, and the product was eluted with a linear gradient from 0 to 100% ANX-Buffer B (10 mM Tris, 1 M NaCl, pH 7.5). Fractions containing the glycoprotein were pooled, the phosphate concentration was adjusted to 5 mM with 500 mM NaH$_2$PO$_4$, and conductivity was adjusted to 10 mS/cm with 5 mM phosphate buffer pH 7.2. The sample was loaded onto a 14 mL ceramic hydroxyapatite type I (Bio-Rad Laboratories) column, washed with 6 CV HA-Buffer A (10 mM sodium phosphate, 100 mM NaCl, pH 6.8), and eluted with a linear gradient from 0 to 100% HA-Buffer B (10 mM sodium phosphate, 1 M NaCl, pH 6.8) over 12 CV. Fractions containing the glycoprotein were pooled and concentrated to 12 mL over a 5 kDa PES Pellicon tangential flow filtration membrane (Millipore). SEC was performed as described for CPS-EPA.

CP8-EPA was purified with four chromatography steps, starting with IMAC, followed by two anion exchange chromatography steps, and finally size exclusion chromatography. The periplasmic extracts, supplemented with 30 mM Tris pH 8, 500 mM NaCl, and 10 mM imidazole pH 8, were loaded on 5 ml HisTrap columns (GE Healthcare). The columns were washed with 5 CV HisTrap wash buffer (30 mM Tris pH 8, 200 mM NaCl, 10 mM imidazole), followed by elution with 100% HisTrap elution buffer (30 mM Tris pH 8, 200 mM NaCl, 500 mM imidazole). The fractions were analyzed by SDS-PAGE, and those containing the glycoprotein were pooled and diluted in Pa11Q buffer A (20 mM L-His pH 6.0) to 5 mS/cm. The diluted samples were loaded onto 10 mL Q Ceramic HyperD F (Pall AG) chromatography columns, washed with 5 CV of PallQ buffer A, and eluted with a 20 CV linear gradient from 0% to 100% PallQ buffer B (20 mM L-His pH 6.0, 1 M NaCl). Fractions were analysed by SDS-PAGE, and those containing the glycoconjugate were pooled and diluted in SourceQ buffer A (20 mM BisTris pH 6.0) to 5 mS/cm. The diluted sample was loaded onto a 10 ml Source 15Q (GE Healthcare) chromatography column, washed with 5 CV of SourceQ buffer A, and eluted with a 20 CV linear gradient from 0% to 100% SourceQ buffer B (20 mM Bis Tris pH 6.0, 1 M NaCl). Fractions were analyzed by SDS-PAGE, and those containing the glycoconjugate were pooled and concentrated to 0.5 ml using an Amicon Ultra-4 Centrifugal Filter Unit with an Ultracel-30 membrane (Millipore). The sample was loaded on a Superdex 200 10/300 GL prepacked gel filtration column (GE Heathcare). Fractions resulting from isocratic elution with 1× PBS were analyzed by SDS-PAGE, and those containing the glycoprotein were pooled and stored at 4° C.

The homogenate containing *Shigella flexneri* 2a-EPA was clarified by tangential flow filtration over a 500 kDa mPES hollow fiber (Spectrum) and purified over Q Ceramic HyperD F (Pall) chromatography matrix, followed by a second anion exchange purification step with Source 15Q beads (GE Healthcare). SEC as described for CPS-EPA was performed as the final purification step. *S. dysenteriae* O1-EPA was purified by two anion exchange chromatography steps with Source 15Q beads as matrix, followed by a SEC step as described for CP5-EPA.

The endotoxin content of the *S. aureus* vaccines and the control *Shigella* vaccines were comparable, ranging from 39-557 EU/mg protein and averaging 155 EU/mg protein.

TABLE 1

Bacterial strains, plasmids, and primers used for the construction of bioconjugate vaccines

| Name | Description | Reference |
|---|---|---|
| Bacterial strains | | |
| *P. aeruginosa* DSM1117 | Exoprotein A positive | DSMZ[a] |
| *P. aeruginosa* | Wild type IATS O11 | [13] |

TABLE 1-continued

Bacterial strains, plasmids, and primers used for the construction of bioconjugate vaccines

| Name | Description | Reference |
|---|---|---|
| PA103 | | |
| S. aureus Mu50 | CP5+ | NARSA[b] |
| S. aureus MW2 | CP8+ | NARSA |
| E. coli DH5a | K-12 φ80dlacZΔM15 endA1 recA1 hsdR17(rK-mK+) supE44 thi-1 gyrA96 relA1 Δ(lacZYA-argF)U169 F- | Clontech |
| E. coli W3110 | Rph-1 IN(rrnD-rrnE)1☐ | CGSC 4474[c] |
| E. coli StGVXN1690 | W3110 ΔwaaL ΔrmlB-wecG::cat | This study |
| E. coli StGVXN1717 | W3110 ΔwaaL ΔwecA-wzzE ΔrmlB-wecG::cat | This study |
| Plasmids | | |
| pLAFR1 | Low copy-number cosmid cloning vector; Tet[r] | [7] |
| pEXT21 | tac promoter expression vector; Spc[r] | [8] |
| pKD3 | PCR template for insertion cassette amplification; Ampr Cmr | [9] |
| pKD46 | λ Red recombinase genes, arabinose inducible; Amp[r] | [9] |
| p336 | pLAFR1 with multiple cloning site inserted in EcoRI site; Tet[r] | This study |
| p341 | pGVXN336 derivative carrying O11 O antigen gene cluster of P. aeruginosa PA102 on an Bsu36I/PciI fragment; Tet[r] | This study |
| p345 | pGVXN341 derivative with O11 wbjA-wzy genes replaced with the cap5HIJ genes of S. aureus strain Mu50; Tet[r] | This study |
| p393 | pGVXN345 with cap5K downstream of cap5HIJ genes; Tet[r] | This study |
| p484 | pGVXN393 derivative carrying pglB cloned into PscI; Tet[r] | This study |
| p404 | pGVXN345 derivative where cap5HIJ genes are replaced with the cap8HIJK genes of S. aureus strain MW2; Tet[r] | This study |
| p405 | pGVXN345 derivative where cap5HIJ genes are replaced with chemically synthesized S. aureus cap8HIJ genes; Tet[r] | This study |
| p413 | pGVXN405 carrying cap8K gene as a Alw44I fragment; Tet[r] | This study |
| p555 | pGVXN413 derivative carrying multiple cloning site inserted in Eco81I and BspTI; Tet[r] | This study |
| p564 | pGVXN555 derivative carrying a constitutive promoter on a SanDI/BspTI fragment; Tet[r] | This study |
| p70 | Soluble periplasmic His$_6$-tagged toxoid variant (L552V, DE553) of P. aeruginosa Epa cloned in pEC415, arabinose inducible; Amp[r] | This study |
| p88 | pGVXN70 derivative containing SmaI site; Amp[r] | This study |

TABLE 1-continued

Bacterial strains, plasmids, and primers used for the construction of bioconjugate vaccines

| Name | Description | Reference |
|---|---|---|
| p137 | pGVXN88 derivative carrying one engineered N-glycosylation site on a Sural fragment; Amp$^r$ | |
| p150 | pGVXN137 derivative carrying two engineered N-glycosylation sites; Amp$^r$ | This study |
| p570 | Soluble periplasmic His$_6$-tagged detoxified Hla (H35L) with one N-glycosylation site cloned in pEC415, arabinose inducible, Amp$^r$ | This study |
| p114 | HA-tagged pglB cloned in pEXT21, IPTG inducible, Spc$^r$ | +11+ |
| Primers | | |
| P1-F | ATTAATGAAAAAGATTTGGCTGGCGCTGGCTGGTTTAGTTTTAGCGT TTAGCGCTAGCGCGTACCCATACGACGTCCCAGACTACGC (SEQ ID NO: 2) | |
| P1-R | AGAATTCTTAAACACTGGCGTCAAAGTGGACAGG (SEQ ID NO: 3) | |
| P2-F | AAGCTAGCGCCGCCGAGGAAGCCTTCGACC (SEQ ID NO: 4) | |
| P2-R | AAGAATTCTCAGTGGTGGTGGTGGTGGTGCTTCAGGTCCTCGCGCG GCGG (SEQ ID NO: 5) | |
| P3-F | GAAGGCGGGCGCGTGACCATTCTCGGC (SEQ ID NO: 6) | |
| P3-R | GCCGAGAATGGTCACGCGCCCGCCTTC (SEQ ID NO: 7) | |
| P4-F | CCGCGCATTCCCCGGGGCAGGTCAGG (SEQ ID NO: 8) | |
| P4-R | CCTGACCTGCCCCGGGGAATGCGCGG (SEQ ID NO: 9) | |
| P5-F | TTTAGTTCTATTTTGATCTTTGGCGAC (SEQ ID NO: 10) | |
| P5-R | GTCGCCAAAGATCAAAATAGAACTAAA (SEQ ID NO: 11) | |
| P6-F | CATGACCTGGACATCAAGGATAATAATAATTCTACTCCCACGGTCA TCAGTCATC (SEQ ID NO: 12) | |
| P6-R | GATGACTGATGACCGTGGGAGTAGAATTATTATTATCCTTGATGTCC AGGTCATG (SEQ ID NO: 13) | |
| P7-F | AATTCACATGTGTGCACCTTAAGCCTCAGGG (SEQ ID NO: 14) | |
| P7-R | AATTCCCTGAGGCTTAAGGTGCACACATGTG (SEQ ID NO: 15) | |
| P8-F | CTGCCTGAGGCAATTCTTCTTTGATGACGGCTGATGG (SEQ ID NO: 16) | |
| P8-R | ACGTACATGTTGCCCATCCACGAAACCACCTTATCGCCG (SEQ ID NO: 17) | |
| P9-F | GTTAGCGCTAGCAGGAGGGACGATGAGGATAGCGATTGAAAAG (SEQ ID NO: 18) | |
| P9-R | CATTTCTAGATTACGCATAATCCGGCACATCATACGGATAACTAGT ATCCTTTTTATTTAAATATTC (SEQ ID NO: 19) | |
| P10-F | GGGGTACCAGGAGGTGTACAATGAGAATTTTAAATATTGTATCGAG GGGGTACCAGGAGGTGTACAATGAGAATTTTAAATATTGTATCGAG (SEQ ID NO: 20) | |
| P10-R | CCGGATCCCAGATCCTCTTCTGAGATGAGTTTTTGTTCAAATTTATA TAATTCTACTAATCGTTCAC (SEQ ID NO: 21) | |
| P11-F | CGTGTTGCTAGCAGGAGGAACTATGAAATTTTTTGTACTTTGTGC (SEQ ID NO: 22) | |
| P11-R | GGCCTTTCTAGATTATTTATCATCATCATCTTTATAATCACCATGAT GACGCCGTCCTTTTG (SEQ ID NO: 23) | |

TABLE 1-continued

Bacterial strains, plasmids, and primers used for the construction of bioconjugate vaccines

| Name | Description | Reference |
|---|---|---|
| P12-F | GGACGCTGGTCGTTACAGAGGTCTCTTTGGGGATGGGAATGTTTTTC CTGGCCACGGTTAAGTTGAGAGAGAAAAGGGGACTTTGACTTAAGA TGAGGATAGCGATTGAAAAG (SEQ ID NO: 24) | |
| P12-R | CTCATTGTACACCTCCTGTTACGCATAATCCGGCACATCATACGG (SEQ ID NO: 25) | |
| P13-F | CAGGAGGTGTACAATGAGAATTTTAAATATTG (SEQ ID NO: 26) | |
| P13-R | CTAAGGAGGATATTCATATGGTGCACGGAAGTTTAAACTTATTTAT CATCATCATCTTTATAATCACCATGATGACGC (SEQ ID NO: 27) | |
| P14-F | GGACGCTGGTCGTTACAGAGGTCTC (SEQ ID NO: 28) | |
| P14-R | CTAAGGAGGATATTCATATGGTGCACGGAAGTTTAAACTTATTTAT CATCATCATCTTTATAATCACCATGATGACGC (SEQ ID NO: 29) | |
| P15-F | CATATGAATATCCTCCTTAG (SEQ ID NO: 30) | |
| P15-R | CTTCAAAACGGCATTTCCAAAGGAACCAGTTCCACCGGTAATTAAC AGAACAGAGTTCTTATCCAT ACACCACCTCTTTACGTGTAGGCTGGAGCTGCTTC (SEQ ID NO: 31) | |
| P16-F | GGACGCTGGTCGTTACAGAGGTCTC (SEQ ID NO: 32) | |
| P16-R | CTTCAAAACGGCATTTCCAAAGG (SEQ ID NO: 33) | |
| P17-F | ACGAGTTTAAACAGGAGGCATCATGGTTAAGAAAGTTTTTATTATG G (SEQ ID NO: 34) | |
| P17-R | CCGCGTGCACTTACGCATAATCCGGCACATCATACGGATAACTATC GACGTCCTTTTTATTAATG (SEQ ID NO: 35) | |
| P18-F | AGGTACATGTCGCGAAGGTAAAGTCAGCCGCATTG (SEQ ID NO: 36) | |
| P18-R | TTGCTAGCGCTGTCGCTTATCATGTAGCGCTTAAATAGCC (SEQ ID NO: 37) | |
| P19-F | ACATGATAAGCGACAGCGCTAGCAATCAAATCTTTTAAAGTTACTT CTCAGGAATAGTAAAAGGAGGACAGCTATGTTGAAAAAAGAGTAT TTAAAAAACC (SEQ ID NO: 38) | |
| P19-R | CGGCGGACATGTTTAAGCGTAATCTGGAACATCGTATGGGTA (SEQ ID NO: 39) | |
| P20-F | AGGTACATGTCGCGAAGGTAAAGTCAGCCGCATTG (SEQ ID NO: 40) | |
| P20-R | CGGCGGACATGTTTAAGCGTAATCTGGAACATCGTATGGGTA (SEQ ID NO: 41) | |
| P21-F | TCGGAGTGCACGAAGAAAATTATGAGATTAAATAAATTTATTGGC (SEQ ID NO: 42) | |
| P21-R | CCGGGTGCACTTACGCATAATCCGGCACATCATACGGATAACTAGA ATTTTTGAACTGTTTATTTTTAGC (SEQ ID NO: 43) | |
| P22-F | TGAGGAATGGGTCCCTATGCGATCGCAAGGCCGGCCTATC (SEQ ID NO: 44) | |
| P22-R | TTAAGATAGGCCGGCCTTGCGATCGCATAGGGACCCATTCC (SEQ ID NO: 45) | |
| P23-F | GTCCCCTGATAGCTAGCTCAGTCCTAGGGATTATGCTAGCTACTAG AGATTAAAGAGGAGAAAC (SEQ ID NO: 46) | |
| P23-R | TTAAGTTTCTCCTCTTTAATCTCTAGTAGCTAGCATAATCCCTAGGA CTGAGCTAGCTATCAGGG (SEQ ID NO: 47) | |
| P24-F | GTCAAGCAGTTTTGGAAAAGTTATCATCATTATAAAGGTAAAACCC ATATGAATATCCTCCTTAG (SEQ ID NO: 48) | |
| P24-R | AGATAAGAAGTGAGTTTTAACTCACTTCTTAAACTTGTTTATTCGTG TAGGCTGGAGCTGCTTC (SEQ ID NO: 49) | |

TABLE 1-continued

Bacterial strains, plasmids, and primers used for the construction of bioconjugate vaccines

| Name | Description | Reference |
|---|---|---|
| P25-F | ATAGTCAGTTCAAAGTTATCAATGGCGACAATGTCCATCAGCAGTA TGTCGTCGATGCCAAAGGAGTCTGGCGCTGACATATGAATATCCTC CTTAG (SEQ ID NO: 50) | |
| P25-R | TGAATGCTTTGTGTAATAAAAAAGCAGACAGGCGACGGAGTGACC ACTCCGTCGCTTTACAAAGAGAGGAAAAGTGTAGGCTGGAGCTGC TTC (SEQ ID NO: 51) | |
| P26-F | CTTCGTGGTTATACTTCTGCTAATAATTTTCTCTGAGAGCATGCATT CATATGAATATCCTCCTTAG (SEQ ID NO: 52) | |
| P26-R | GATTCTCTTCGAATAAGCGGCGAGCGCCTTTGCGCTCACCGCAGCA GTGTTGGTGTAGGCTGGAGCTGCTTC (SEQ ID NO: 53) | |

[a]DSMZ, German Collection of Microorganisms and Cell Cultures, Leibniz-Institut, Braunschweig, Germany
[b]NARSA, The Network on Antimicrobial Resistance in *Staphylococcus aureus*
[c]The Coli Genetic Stock Center, Yale University, New Haven, CT, USA
Abbreviations: Tet, tetracycline; Spc, spectinomycin; Amp, ampicillin; Cm, chloramphenicol.

REFERENCES

1. Killeen K P, Collier R J. Conformational integrity of a recombinant toxoid of *Pseudomonas aeruginosa* exotoxin A containing a deletion of glutamic acid-553. Biochim Biophys Acta 1992; 1138:162-6.
2. Kowarik M, Young N M, Numao S, et al. Definition of the bacterial N-glycosylation site consensus sequence. EMBO J 2006; 25:1957-66.
3. Geiger R, Gautschi M, Thor F, Hayer A, Helenius A. Folding, quality control, and secretion of pancreatic ribonuclease in live cells. J Biol Chem 2011; 286:5813-22.
4. Jursch R, Hildebrand A, Hobom G, et al. Histidine residues near the N terminus of staphylococcal alpha-toxin as reporters of regions that are critical for oligomerization and pore formation. Infect Immun 1994; 62:2249-56.
5. Menzies B E, Kernodle D S. Site-directed mutagenesis of the alpha-toxin gene of *Staphylococcus aureus*: role of histidines in toxin activity in vitro and in a murine model. Infect Immun 1994; 62:1843-7.
6. Song L, Hobaugh M R, Shustak C, Cheley S, Bayley H, Gouaux J E. Structure of staphylococcal alpha-hemolysin, a heptameric transmembrane pore. Science 1996; 274: 1859-66.
7. Friedman A M, Long S R, Brown S E, Buikema W J, Ausubel F M. Construction of a broad host range cosmid cloning vector and its use in the genetic analysis of *Rhizobium* mutants. Gene 1982; 18:289-96.
8. Dykxhoorn D M, St Pierre R, Linn T. A set of compatible tac promoter expression vectors. Gene 1996; 177:133-6.
9. Datsenko K A, Wanner B L. One-step inactivation of chromosomal genes in *Escherichia coli* K-12 using PCR products. Proc Natl Acad Sci USA 2000; 97:6640-5.
10. Wetter M, Kowarik M, Steffen M, Carranza P, Corradin G, Wacker M. Engineering, conjugation, and immunogenicity assessment of Escherichia *coli* O121 O antigen for its potential use as a typhoid vaccine component. Glycoconj J 2013; 30:511-22.
11. Ihssen J, Kowarik M, Dilettoso S, Tanner C, Wacker M, Thony-Meyer L. Production of glycoprotein vaccines in *Escherichia coli*. Microb Cell Fact 2010; 9:61.
12. Meier-Dieter U, Starman R, Barr K, Mayer H, Rick P D. Biosynthesis of enterobacterial common antigen in *Escherichia coli*. Biochemical characterization of Tn10 insertion mutants defective in enterobacterial common antigen synthesis. J Biol Chem 1990; 265:13490-7.
13. Liu P V, Yoshii S, Hsieh H. Exotoxins of *Pseudomonas aeruginosa*. II. Concentration, purification, and characterization of exotoxin A. J Infect Dis 1973; 128:514-9.

Equivalents and Incorporation by Reference: The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following embodiments. All references (including patent applications, patents, and publications) cited herein are incorporated herein by reference in their entireties and for all purposes to the same extent as if each individual publication or patent or patent application was specifically and individually indicated to be incorporated by reference in its entirety for all purposes.

The invention claimed is:

1. A composition comprising a capsular polysaccharide type 8 that is N-linked to clumping factor A (CP8-ClfA), and a second N-glycosylated protein, wherein said clumping factor A comprises one or more recombinantly introduced N-glycosylation consensus sequences and wherein said second N-glycosylated protein is a capsular polysaccharide type 5 alpha toxin (CP5-Hla).

2. The composition of claim 1 further comprising a third N-glycosylated protein.

3. The composition of claim 2, wherein the third N-glycosylated protein is CP5-Epa, CP8-Epa, CP5-ClfA, or CP8-Hla.

4. A method of treating an infection with *Staphylococcus aureus* in an animal, comprising a step of administering an immunogenic amount of the composition of claim 1 to said animal.

5. The method of claim 4 wherein the *Staphylococcus aureus* is Methicillin-resistant *Staphylococcus aureus* (MRSA).

6. A method of eliciting an antibody response against *Staphylococcus aureus* in an animal, comprising a step of administering an immunogenic amount of the composition of claim 1 to said animal.

7. The method of claim 4, wherein the animal is a human.

8. The method of claim 6, wherein the animal is a human.

* * * * *